US007319111B2

(12) United States Patent
Gao et al.

(10) Patent No.: US 7,319,111 B2
(45) Date of Patent: Jan. 15, 2008

(54) PHENYLENEDIAMINE UROTENSIN-II RECEPTOR ANTAGONISTS AND CCR-9 ANTAGONISTS

(75) Inventors: Daxin Gao, Houston, TX (US); Robert Market, Pearland, TX (US); Chengde Wu, Pearland, TX (US)

(73) Assignee: Encysive Pharmaceuticals, Inc., Houston, TX (US)

( * ) Notice: Subject to any disclaimer, the term of this patent is extended or adjusted under 35 U.S.C. 154(b) by 35 days.

(21) Appl. No.: 10/781,442

(22) Filed: Feb. 18, 2004

(65) Prior Publication Data

US 2004/0180892 A1    Sep. 16, 2004

(51) Int. Cl.
*A61K 31/381* (2006.01)
*C07D 409/12* (2006.01)

(52) U.S. Cl. .......................... 514/444; 549/29; 549/59; 514/438

(58) Field of Classification Search ................ 514/422, 514/445, 447, 448, 438, 444; 548/527; 549/64, 549/72, 29, 59
See application file for complete search history.

(56) References Cited

U.S. PATENT DOCUMENTS

| 5,019,587 | A |   | 5/1991  | Von der Saal et al. |         |
|-----------|---|---|---------|---------------------|---------|
| 5,932,599 | A |   | 8/1999  | Bos et al.          |         |
| 5,962,490 | A | * | 10/1999 | Chan et al.         | 514/380 |
| 5,998,439 | A |   | 12/1999 | Maynard et al.      |         |
| 6,335,334 | B1| * | 1/2002  | Schindler et al.    | 514/231.5 |
| 6,395,759 | B1|   | 5/2002  | Thompson et al.     |         |
| 6,420,567 | B1| * | 7/2002  | Wu et al.           | 548/245 |
| 6,632,829 | B2| * | 10/2003 | Wu et al.           | 514/361 |
| 2003/0064991 | A1 | * | 4/2003 | Harriman et al.   | 514/243 |
| 2005/0049286 | A1 | * | 3/2005 | Wu et al.         | 514/357 |

FOREIGN PATENT DOCUMENTS

| EP | 0 344 634 A1 | 5/1989 |
| EP | 0 533 266 A1 | 9/1992 |
| EP | 0 533 267 A1 | 9/1992 |
| EP | 0 533 268 A1 | 9/1992 |
| EP | 0 815 861 A1 | 1/1998 |
| EP | 1 104 763 A1 | 8/1999 |
| WO | WO 94/22807 A1 | 10/1994 |
| WO | WO 9813366 A1 * | 4/1998 |
| WO | WO 00/27820 A1 | 5/2000 |
| WO | WO 200149289 A1 * | 7/2001 |
| WO | WO 0228353 A2 * | 4/2002 |
| WO | WO 200228353 A2 * | 4/2002 |
| WO | WO 02/089740 A2 | 11/2002 |
| WO | WO 02/089785 A1 | 11/2002 |
| WO | WO 02/089792 A1 | 11/2002 |
| WO | WO 02/089793 A1 | 11/2002 |
| WO | WO 02/090337 A1 | 11/2002 |
| WO | WO 02/090348 A1 | 11/2002 |
| WO | WO 02/090353 A1 | 11/2002 |
| WO | WO 03/099773 A1 | 12/2003 |
| WO | WO 2004/026836 A2 | 4/2004 |

OTHER PUBLICATIONS

Cohn, J. "The Management of Chronic Heart Failure," N. Engl. J. Med., vol. 335(7), pp. 490-498 (Aug. 1996) at p. 493, col. 2, line 47 (Table 2).*
Wu et al., J. Med. Chem. vol. 42, pp. 4485-4499 (1999).*
Wu, et al., J. Med. Chem. (1999), vol. 42, pp. 4485-4499.*
Silverman, R.B., "The Organic Chemistry of Drug Design and Drug Action" pp. 15-22 (1992).

* cited by examiner

*Primary Examiner*—Golam M. M. Shameem
(74) *Attorney, Agent, or Firm*—Jones Day

(57) ABSTRACT

The present invention relates to urotensin II receptor antagonists, CCR-9 antagonists, pharmaceutical compositions containing them and their use.

4 Claims, No Drawings

PHENYLENEDIAMINE UROTENSIN-II RECEPTOR ANTAGONISTS AND CCR-9 ANTAGONISTS

FIELD OF THE INVENTION

The present invention relates to urotensin II receptor antagonists, pharmaceutical compositions containing them and their use.

BACKGROUND OF THE INVENTION

The integrated control of cardiovascular homeostasis is achieved through a combination of both direct neuronal control and systemic neurohormonal activation. Although the resultant release of both contractile and relaxant factors is normally under stringent regulation, an aberration in this status quo can result in cardiohemodynamic dysfunction with pathological consequences.

The principal mammalian vasoactive factors that comprise this neurohumoral axis are angiotensin-II, endothelin-1, and norepinephrine, all of which function via an interaction with specific G-protein coupled receptors (GPCR). Urotensin-II, represents an important member of this neurohumoral axis.

In the fish, this peptide has significant hemodynamic and endocrine actions in diverse end-organ systems and tissues: both vascular and non-vascular (smooth muscle contraction)
  including smooth muscle preparations from the gastrointestinal tract and genitourinary tract. Both pressor and depressor activity has been described upon systemic administration of exogenous peptide.
osmoregulation effects which include the modulation of transepithelial ion ($Na^+$, $Cl^-$) transport.

Although a diuretic effect has been described, such an effect is postulated to be secondary to direct renovascular effects (elevated GFR); urotensin-II influences prolactic secretion and exhibits a lipolytic effect in fish (activating triacylglycerol lipase resulting in the mobilization of non-esterified free fatty acids) (Person, et al. *Proc. Natl. Acad. Sci.* (*U.S.A.*) 1980, 77, 5021; Conlon, et al. *J. Exp. Zool.* 1996, 275, 226); human Urotensin-II has been found to be an extremely potent and efficacious vasoconstrictor; exhibited sustained contractile activity that was extremely resistant to wash out; and had detrimental effects on cardiac performance (myocardial contractility). Human Urotensin-II was assessed for contractile activity in the rat-isolated aorta and was shown to be a very potent contractile agonist. Based on the in vitro pharmacology and in vivo hemodynamic profile of human Urotensin-II, it plays a pathological role in cardiovascular diseases characterized by excessive or abnormal vasoconstriction and myocardial dysfunction. (Ames et al. *Nature* 1990, 401, 282.)

Compounds that antagonize the Urotensin-II receptor may be useful in the treatment of congestive heart failure, stroke, ischemic heart disease (angina, myocardial ischemia), cardiac arrhythmia, hypertension (essential and pulmonary), COPD, fibrosis (e.g. pulmonary fibrosis), restenosis, atherosclerosis, dyslipidemia, asthma, neurogenic inflammation and metabolic vasculopathies all of which are characterized by abnormal vasoconstriction and/or myocardial dysfunction. Urotensin antagonists may provide end organ protection in hypersensitive cohorts in addition to lowering blood pressure.

Since Urotensin-II and GPR 14 are both expressed within the mamamalian CNS (Ames et al. *Nature* 1999, 401, 282), they also may be useful in the treatment of addiction, schizophrenia, cognitive disorders/Alzheimers disease, impulsivity, anxiety, stress, depression, pain, migraine, neuromuscular function, Parkinsons, movement disorders, sleep-wake cycle, and incentive motivation.

Functional Urotensin-II receptors are expressed in rhabdomyosarcomas cell lines and therefore may have oncological indications. Urotensin may also be implicated in various metabolic diseases such as diabetes and in various gastrointestinal disorders, bone, cartilage, and joint disorders (e.g., arthritis and osteoporosis); and genito-urinary disorders. Therefore, these compounds may be useful for the prevention (treatment) of gastric reflux, gastric motility and ulcers, arthritis, osteoporosis and urinary incontinence.

CCR-9, a seven transmembrane, G-protein-coupled chemokine receptor was recently identified as the physiologic receptor for CCL25/thymus-expressed Chemokine (TECK). CCR-9 is mainly expressed in thymocytes and T lymphocytes from the small intestine and colon. CCL25/TECK is predominantly expressed in the thymus and small intestine. Studies have shown that CCR-9 mediates chemotaxis in response to CCL25/TECK is likely to play an important role in regulating the trafficking of developing T cells within the thymus and be critical for the development, homeostasis, and/or function of mucosal T lymphocytes.

It has been shown that CCR-9+ lymphocytes were markedly elevated in peripheral blood lymphocytes in patients with small bowl Crohn's or celiac disease. TECK expression is altered in an inflamed small bowel, being intensely expressed in a patchy distribution in crypt epithelial cells in proximity to lymphocytic infiltrates. Neutralization of TECK inhibits homing of CD8+ T cells to the IEL (intraepithelial lymphocyte) compartment. This directly demonstrates that CCL25 and CCR-9 function in recruiting effector lymphocytes to the small intestinal epithelium following their activation in gut-associated lymphoid tissue (GALT).

Targeting CCL25/TECK and/or CCR-9 may provide a way to selectively modulate small-intestinal immune responses as suggested by the fact that activated CCR-9(+) CD8alphabeta(+) lymphocytes selectively localized to the small-intestinal mucosa, and in vivo neutralization of CCL25/TECK reduced the ability of these cells to populate the small-intestinal epithelium These results demonstrate an important role for chemokines in the localization of T lymphocytes to the small-intestinal mucosa. (Svensson et al., J. Clin. Invest., 2002, 110:1113-21)

CCR-9 receptor expression on human eosinophils from peripheral blood and bronchoalveolar lavage fluid after setmental antigen challenge was reported recently (Liu et al, J Allergy Clin Immunol. 2003 September; 112(3):556-62). CCR-9 was also found to selectively express on T-ALL CD4+ T cells and moderately express on T-CLL CDR+ T cells. CCL25/TECK selectively induced T-ALL CD4+ T cell chamotaxis and adhesion (Qiuping et al., Cancer Res. 2003 Oct. 1; 63(19):6469-77. Annels et al., Blood 2003 Dec. 4 [Epub ahead of print]). A recent study also demonstrates an increase in the expression of CCR-9 on peripheral blood gammadelta T cells in individuals having HIV-1 infection (Poles et al., J Virol. 2003 October; 77(19):10456-67).

SUMMARY OF THE INVENTION

In one aspect this invention provides for compounds and pharmaceutical compositions containing them.

In a second aspect, this invention provides for the use of these compounds as antagonists of urotensin II, and as inhibitors of urotensin II.

In another aspect, this invention provides for the use of these compounds for treating conditions associated with urotensin II imbalance.

In yet another aspect, this invention provides for the use of these compounds for the treatment of congestive heart failure, stroke, ischemic heart disease (angina, myocardial ischemia), cardiac arrhythmia, hypertension (essential and pulmonary), renal disease (acute and chronic renal failure/end stage renal disease) along with peripheral vascular disease (male erectile dysfunction, diabetic retinopathy, intermittent claudication/ischemic limb disease) and ischemic/hemorrhage stroke, COPD, restenosis, asthma, neurogenic inflammation, migraine, metabolic vasculopathies, bone/cartilage/joint disease, arthritis and other inflammatory diseases, fibrosis (e.g. pulmonary fibrosis), sepsis atherosclerosis, dyslipidemia, addiction, schizophrenia, cognitive disorders/Alzheimers disease, impulsivity, anxiety, stress, depression, parkinsons, movement disorders, sleep-wake cycle, incentive motivation, pain, neuromuscular function, diabetes, gastric reflux, gastric motility disorders, ulcers and genitourinary diseases.

The urotensin antagonist may be administered alone or in conjunction with one or more other therapeutic agents, said agents being selected from the group consisting of endothelin receptor antagonists, angiotensin converting enzyme (ACE) inhibitors, A-II receptor antagonists, vasopeptidase inhibitors, diuretics, digoxin, and dual non-selective β-adrenoceptor and α$_1$-adrenoceptor antagonists.

In yet another aspect, the present invention provides compounds that are CCR-9 antagonists, the use of these compounds as CCR-9 antagonists and the treatment of conditions associated with CCR-9 such as Crohn's disease, celiac disease and other forms of intestinal inflammation.

Other aspects and advantages of the present invention are described further in the following detailed description of the preferred embodiments thereof.

DETAILED DESCRIPTION OF THE INVENTION

The present invention provides for compounds of Formula (I):

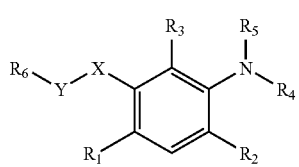

Formula (I)

wherein:
$R_1$, $R_2$ and $R_3$ are independently selected from the group consisting of hydrogen, halogen, $C_{1-6}$ alkyl, aryl, aralkyl, CN, $CF_3$ arene sulfonyl, $C_{1-6}$ alkanesulfonyl, $C_{1-6}$ alkanecarbonyl, $CONR_7R_8$ and $CO_2R_9$;
X is N, $CH_2$, or O;
Y is selected from the group consisting of $SO_2$, CO, $CH_2SO_2$, $CH_2CO$, NHCO, OCO and $NHSO_2$;
$R_4$ is selected from the group consisting of $C_{1-6}$ alkyl, aryl, aralkyl, and heteroaryl;
$R_5$ is the same as $R_1$ or $Z$-$NR_7R_8$ or $R_4$ and $R_5$ taken with N can form a 5 or 6 membered ring;
Z is $(CH_2)_n$ where n is 0-6;

$R_6$ s selected from the group consisting of aryl, heteroaryl and $ZNR_7R_8$;
$R_7$ and $R_8$ are independently selected from the group consisting of hydrogen, lower alkyl, aryl, and aralkyl or together with N form a pyrrolidine, piperizine, piperidine or morpholine ring; and
$R_9$ is selected from the group consisting of hydrogen, $c_{1-6}$ alkyl, aryl, aralkyl, and the pharmaceutically acceptable salts thereof.

Preferably $R_1$, $R_2$ and $R_3$ are each methyl or $R_1$ and $R_2$ are methyl and $R_3$ is hydrogen; X is N, Y is $SO_2$ and $R_1$ is 3,5-dichloro-2-hydroxybenzene.

In another embodiment, the CCR-9 antagonist compounds of the present invention have the general formula:

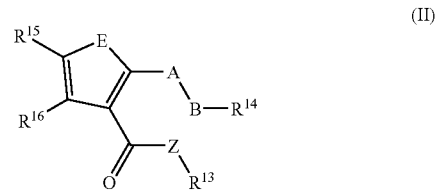

(II)

where E is $NR^{11}$, O, S, $CR^{11}$=$CR^{12}$, or $CR^{11}$=N, where $R^{11}$ and $R^{12}$ are independently alkyl, aryl, hetero-aryl, halogen, hydroxy, alkoxy, or $CONR_2^{11}$;
D is $NR^{10}$, O or S, where $R^{10}$ is H, lower alkyl or aryl or $R^{10}$ may also be taken together with $R^{16}$ or $R^{13}$ to form a ring;
Z is $NR^{13}$ or $CR^{13}_2$ where each $R^{13}$ is independently H, lower alky, aryl or heteroaryl;
A is $NR^{17}$ C=O or $SO_2$, where $R^{17}$ is H, alkyl or aryl and may be taken together with $R^{14}$ to form a ring;
when A is $NR^{17}$, B is $SO_2$, $CO_2$ or $CR^{18}_2$, where each $R^{18}$ is independently H, alkyl, aryl or heteroaryl;
when A is C=O or $SO_2$, B is $NR^{19}$, where $R^{19}$ is H alkyl or aryl and may be taken together with $R^{12}$ to form a ring;
$R^{13}$ and $R^{14}$ are independently H, alkyl, aryl or heteroaryl; and
$R^{15}$ and $R^{16}$ are independently H, alkyl, aryl, heteroaryl, halogen, hydroxy, alkoxy or $NR_2^{21}$, where $R^{21}$ is H, alkyl, aryl or heteroaryl, and the pharmaceutically acceptable salts thereof.

Presently preferred compounds are:
N-(2,4,6-trimethyl-3-pyrrolidin-1-yl-phenyl)-thiophene-2-carboxamide
3-methyl-N-(2,4,6-trimethyl-3-pyrrolidin-1-yl-phenyl)-benzamide
2-chloro-N-(2,4,6-trimethyl-3-pyrrolidin-1-yl-phenyl)-benzamide
N-(2,4,6-trimethyl-3-pyrrolidin-1-yl-phenyl)-biphenyl-2-carboxamide
1-(2-methoxyphenyl)-3-(2,4,6-trimnethyl-3-pyrrolidin-1-yl-phenyl)-urea
4-chloro-N-(2,4,6-trimethyl-3-pyrrolidin-1-yl-phenyl)-benzenesulfonamide
3-phenylaminosulfonyl-N-(2,4,6-trimethyl-3-pyrrolidin-1-yl-phenyl)-thiophene-2-carboxamide
3-benzenesulfonylamino-N-(2,4,6-trimethyl-3-pyrrolidin-1-yl-phenyl)-thiophene-2-carboxamide
1-(4-chlorobenzenesulfonyl)-3-(2,4,6-trimnethyl-3-pyrrolidin-1-yl-phenyl)-urea
N-(4-methyl-3-pyrrolidin-1-yl-phenyl)-biphenyl-2-carboxamide N-(2-methyl-5-pyrrolidin-1-yl-phenyl)-biphenyl-2-carboxamide
N-(2,4,6-trimethyl-3-pyrrolidin-1-yl-phenyl)-benzamide
N-(2,4,6-trimethyl-3-piperidin-1-yl-phenyl)-biphenyl-2-carboxamide
2-bromo-N-(2,4,6-trimethyl-3-pyrrolidin-1-yl-phenyl)-benzamide
2-bromo-5-methoxy-N-(2,4,6-trimethyl-3-pyrrolidin-1-yl-phenyl)-benzamide
2-bromo-5-methyl-N-(2,4,6-trimethyl-3-pyrrolidin-1-yl-phenyl)-benzamide
N-(2,4,6-trimethyl-3-pyrrolidin-1-yl-phenyl)-benzenesulfonamide
2,5-dichloro-N-(2,4,6-trimethyl-3-pyrrolidin-1-yl-phenyl)-benzenesulfonamide
3-(2,4,6-trimethyl-3-pyrrolidin-1-yl-phenylaminosulfonyl)-thiophene-2-carboxylic acid
4-chloro-N-(2,4,6-trimethyl-3-morpholin-4-yl-phenyl)-benzenesulfonamide
4-methoxy-N-(2,4,6-trimethyl-3-pyrrolidin-1-yl-phenyl)-biphenyl-2-carboxamide
4-methyl-N-(2,4,6-trimethyl-3-pyrrolidin-1-yl-phenyl)-biphenyl-2-carboxamide
4'-methoxy-N-(2,4,6-trimethyl-3-pyrrolidin-1-yl-phenyl)-biphenyl-2-carboxamide
2,3-dimethoxy-N-(2,4,6-trimethyl-3-pyrrolidin-1-yl-phenyl)-benzamide
3-chloro-N-(2,4,6-trimethyl-3-pyrrolidin-1-yl-phenyl)-benzamide
2-trifluoromethyl-N-(2,4,6-trimethyl-3-pyrrolidin-1-yl-phenyl)-benzamide
2-hydroxy-4-methyl-N-(2,4,6-trimethyl-3-pyrrolidin-1-yl-phenyl)-benzenesulfonamide
3,5-dichloro-2-hydroxy-N-(2,4,6-trimethyl-3-pyrrolidin-1-yl-phenyl)-benzenesulfonamide
4-hydroxy-N-(2,4,6-trimethyl-3-pyrrolidin-1-yl-phenyl)-benzenesulfonamide
3'-methyl-N-(2,4,6-trimethyl-3-pyrrolidin-1-yl-phenyl)-biphenyl-2-carboxamide
3,5-dichloro-2-hydroxy-N-(2,4,6-trimethyl-3-(4-phenyl-piperizin-1-yl)-phenyl)-benzenesulfonamide
3,5-dichloro-2-hydroxy-N-(2,4,6-trimethyl-3-(piperidin-1-yl)-phenyl)-benzenesulfonamide
3,5-dichloro-2-hydroxy-N-(2-methyl-5-pyrrolidin-1-yl-phenyl)-benzenesulfonamide
3,5-dichloro-2-hydroxy-N-(2-methyl-3-pyrrolidin-1-yl-phenyl)-benzenesulfonamide
3,5-dichloro-2-hydroxy-N-(2,4,6-trimethyl-3-morpholin-4-yl-phenyl)-benzenesulfonamide
3,5-dichloro-2-hydroxy-N-(2,4,6-trimethyl-3-(4-methyl-piperidin-1-yl)-phenyl)-benzenesulfonamide
2-amino-N-(2,4,6-trimethyl-3-pyrrolidin-1-yl-phenyl)-benzenesulfonamide
3,5-dichloro-2-hydroxy-N-(2,4,6-trimethyl-3-(4-methylpiperizin-1-yl)-phenyl)-benzenesulfonamide
2,3-dimethyl-N-(2,4,6-trimethyl-3-pyrrolidin-1-yl-phenyl)-benzamide
3,5-dichloro-N-(3-diethylamino-2,4,6-trimethyl-phenyl)-2-hydroxy-benzenesulfonamide
3,5-dichloro-2-hydroxy-N-(4-pyrrolidin-1-yl-phenyl)-benzenesulfonamide
3,5-dichloro-2-hydroxy-N-(2-pyrrolidin-1-yl-phenyl)-benzenesulfonamide
3,5-dichloro-2-methanesulfonylamino-N-(2,4,6-trimethyl-3-pyrrolidin-1-yl-phenyl)-benzenesulfonamide
3,5-dichloro-2-hydroxy-N-(2,4,6-trimethyl-3-(pyridin-3-ylamino)-phenyl)-benzenesulfonamide
3,5-dichloro-2-hydroxy-N-(4-methyl-3-pyrrolidin-1-yl-phenyl)-benzenesulfonamide
3,5-dichloro-2-hydroxy-N-(2,4,6-trimethyl-3-pyrrolidin-1-yl-phenyl)-benzamide
3,5-dichloro-2-hydroxy-N-(3,4-dimethyl-2-pyrrolidin-1-yl-phenyl)-benzenesulfonamide
3,5-dichloro-2-hydroxy-N-(4,5-dimethyl-2-pyrrolidin-1-yl-phenyl)-benzenesulfonamide
3,5-dichloro-2-hydroxy-N-(3,5-dimethyl-2-pyrrolidin-1-yl-phenyl)-benzenesulfonamide
N-(3-benzylamino-2,4,6-trimethyl-phenyl)-3,5-dichloro-2-hydroxy-benzenesulfonamide
N-(2,4-dichloro-6-(2,4,6-trimethyl-3-pyrrolidin-1-yl-phenylaminosulfonyl)phenyl)-acetamide
3,5-dichloro-N-(2-cyano-3-piperidin-1-yl-phenyl)-2-hydroxy-benzenesulfonamide
2-methoxy-3,5-dimethyl-N-(2,4,6-trimethyl-3-piperidin-1-yl-phenyl)-benzenesulfonamide
N-benzyl-N-(3-benzylamino-2,4,6-trimethyl-phenyl)-3,5-dichloro-2-hydroxy-benzenesulfonamide
3,5-dichloro-N-(3-(1,3-dihydro-isoindol-2-yl)-2,4,6-trimethyl-phenyl)-2-hydroxy benzenesulfonamide
2-hydroxy-3,5-dimethyl-N-(2,4,6-trimethyl-3-piperidin-1-yl-phenyl)-benzenesulfonamide tert-butyl (2-(3,5-dichloro-2-hydroxybenzenesulfonylamino)-6-piperidin-1-yl-benzyl)-carbamate
3,5-dichloro-N-(2-(dimethylamino)-ethyl)-2-hydroxy-N-(2,4,6-triethyl-3-piperidin-1-yl-phenyl)-benzenesulfonamide
N-(2-aminomethyl-3-piperidin-1-yl-phenyl)-3,5-dichloro-2-hydroxy-benzenesulfonamide
1-(2-(4-benzyl-piperazin-1-yl)-ethyl)-3-(2,4,6-trimethyl-3-piperidin-1-yl-phenyl)-urea
1-(2,4,6-trimethyl-3-(4-methyl-piperazin-1-yl)-phenyl)-3-(2,4,6-trimethyl-3-piperidin-1-yl-phenyl)-urea.

The term "alkyl" as used herein, alone or in combination, refers to $C_1$-$C_6$ straight or branched, substituted or unsubstituted saturated chain radicals derived from saturated hydrocarbons by the removal of one hydrogen atom, unless the term alkyl is preceded by a $C_x$-$C_y$ designation. Representative examples of alkyl groups include methyl, ethyl, n-propyl, iso-propyl, n-butyl, sec-butyl, iso-butyl, and tert-butyl among others.

The term "aryl", "arene" or "aromatic" as used herein alone or in combination, refers to a substituted or unsubstituted carbocyclic aromatic group having about 6 to 12 carbon atoms such as phenyl, naphthyl, indenyl, indanyl, azulenyl, fluorenyl and anthracenyl; or a heterocyclic aromatic group which is an aromatic ring containing at least one endocyclic N, O or S atom such as furyl, thienyl, pyridyl, pyrrolyl, oxazolyl, thiazolyl, imidazolyl, pyrazolyl, 2-pyrazolinyl pyrazolidinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, 2,3-dihydrobenzofuranyl, benzo[b]thiophenyl, 1H-indazolyl, benzimidazolyl, benzthiazolyl, purinyl, 4H-quinolizinyl, isoquinolinyl, cinnolinyl, phthalazinyl, quinazolinyl, quinoxalinyl, 1,8-napthridinyl, pteridinyl, carbazolyl, acridinyl, phenazinyl, phenothiazinyl, phenoxyazinyl, pyrazolo[1,5-c]triazinyl and the like. "Aralkyl" and "alkylaryl" employ the term "alkyl" as defined above. Rings may be multiply substituted.

The term "aralkyl" as used herein, alone or in combination, refers to an aryl substituted alkyl radical, wherein the terms "alkyl" and "aryl" are as defined above. Examples of suitable aralkyl radicals include, but are not limited to, phenylnethyl, phenethyl, phenylhexyl, diphenylmethyl, pyridylmethyl, tetrazolyl methyl, furylnethyl, imidazolyl methyl, indolylmethyl, thienylpropyl and the like.

The term "heterocycle" as used herein, alone or in combination, refers to a non-aromatic 3- to 10-membered ring containing at least one endocyclic N, O, or S atom. The heterocycle may be optionally aryl-fused. The heterocycle may also optionally be substituted with at least one substituent which is independently selected from the group consisting of hydrogen, halogen, hydroxyl, amino, nitro, trifluoromethyl, trifluoromethoxy, alkyl, aralkyl, alkenyl, alkynyl, aryl, cyano, carboxy, carboalkoxy, carboxyalkyl, oxo, arylsulfonyl and aralkylaminocarbonyl among others.

The term "halogen" or "halo" as used herein, refers to fluorine, chlorine, bromine and iodine or fluoro, chloro, bromo and iodo, respectively.

The term "optical isomers" as used herein refers to compounds which differ only in the stereochemistry of at least one atom, including enantiomers, diastereomers and racemates.

Use of the above terms is meant to encompass substituted and unsubstituted moieties. Substitution may be by one or more groups such as alcohols, ethers, esters, amides, sulfones, sulfides, hydroxyl, nitro, cyano, carboxy, amines, heteroatoms, lower alkyl, lower alkoxy, lower alkoxycarbonyl, alkoxyalkoxy, acyloxy, halogens, trifluoromethoxy, trifluoromethyl, alkyl, aralkyl, alkenyl, alkynyl, aryl, cyano, carboxy, carboalkoxy, carboxyalkyl, cycloalkyl, cycloalkylalkyl, heterocyclyl, alkylbeterocyclyl, heterocyclylalkyl, oxo, arylsulfonyl and aralkylaminocarbonyl or any of the substituents of the preceding paragraphs or any of those substituents either attached directly or by suitable linkers. The linkers are typically short chains of 1-3 atoms containing any combination of —C—, —C(O)—, —N—H—, —S—, —S(O)—, —O—, —C(O)O— or —S(O)O—. Rings may be substituted multiple times.

The terms "electron-withdrawing" or "electron-donating" refer to the ability of a substituent to withdraw or donate electrons relative to that of hydrogen if hydrogen occupied the same position in the molecule. These terms are well-understood by one skilled in the art and are discussed in *Advanced Organic Chemistry* by J. March, 1985, pp. 16-18, incorporated herein by reference. Electron withdrawing groups include halo, nitro, carboxyl, lower alkenyl, lower alkynyl, carboxaldehyde, carboxyamido, aryl, quaternary ammonium, trifluoromethyl, sulfonyl and aryl lower alkanoyl among others. Electron donating groups include such groups as hydroxy, lower alkyl, amino, lower alkylamnino, di(lower alkyl)amino, aryloxy, mercapto, lower alkylthio, lower alkylmercapto, and disulfide among others. One skilled in the art will appreciate that the aforesaid substituents may have electron donating or electron withdrawing properties under different chemical conditions. Moreover, the present invention contemplates any combination of substituents selected from the above-identified groups.

The most preferred electron donating or electron withdrawing substituents are halo, nitro, alkanoyl, carboxaldehyde, arylalkanoyl, aryloxy, carboxyl, carboxamide, cyano, sulfanyl, sulfoxide, heterocyclyl, guanidine, quaternary ammonium, lower alkenyl, lower alkynyl, sulfonium salts, hydroxy, lower alkoxy, lower alkyl, amino, lower alkylamino, di(lower alkyl)amino, amine lower alkyl mercapto, mercaptoalkyl, alkylthio, carboxy lower alkyl, arylalkoxy, alkanoylamino, alkanoyl (lower alkyl) amino, lower alkyl-sufonylamino, arylsulfonylamino, alkylsulfonyl (lower alkyl) amino, arysulfonyl (lower alkyl) amino, lower alky-lcarboxamide, di(lower alkyl) carboxaride, sulfonamide, lower alkylsulfonamide, di(lower alkyl sulfonamide, lower alkylsulfonyl, arylsulfonyl and alkyldithio.

As used herein, the term "composition" is intended to encompass a product comprising the specified ingredients in the specified amounts, a well as any product which results, directly or indirectly, from a combination of the specified ingredients in the specified amounts.

As used herein, the term "mammals" includes humans and other animals.

Compounds of the present invention may be synthesized according to the following Schemes.

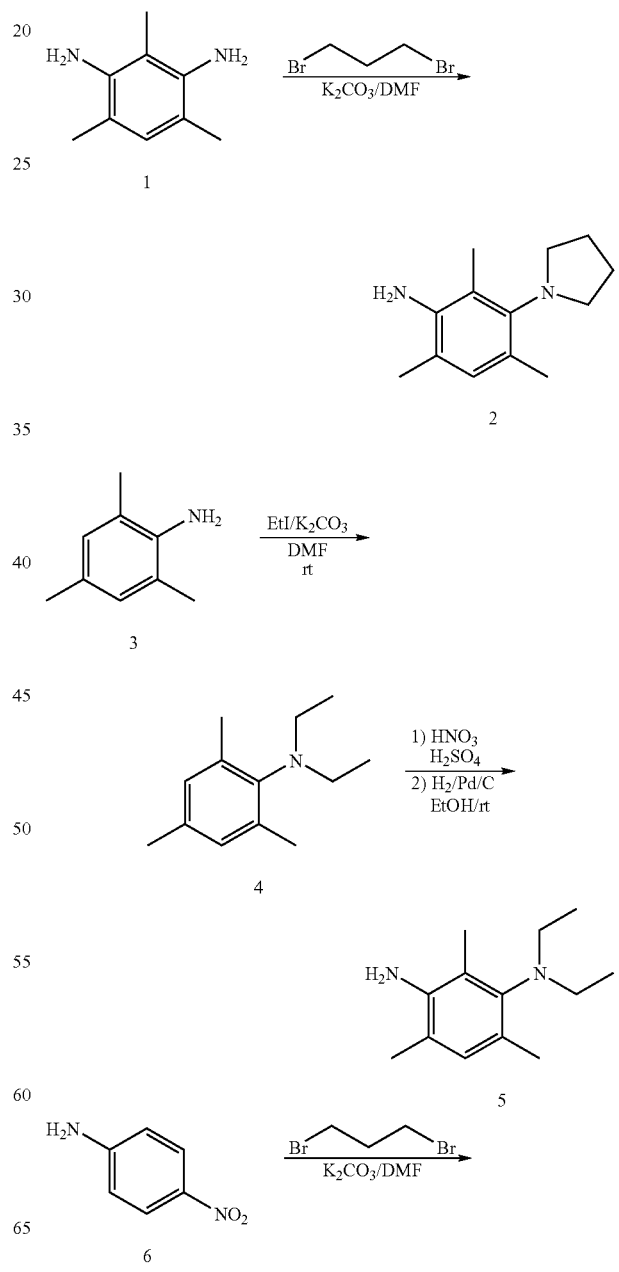

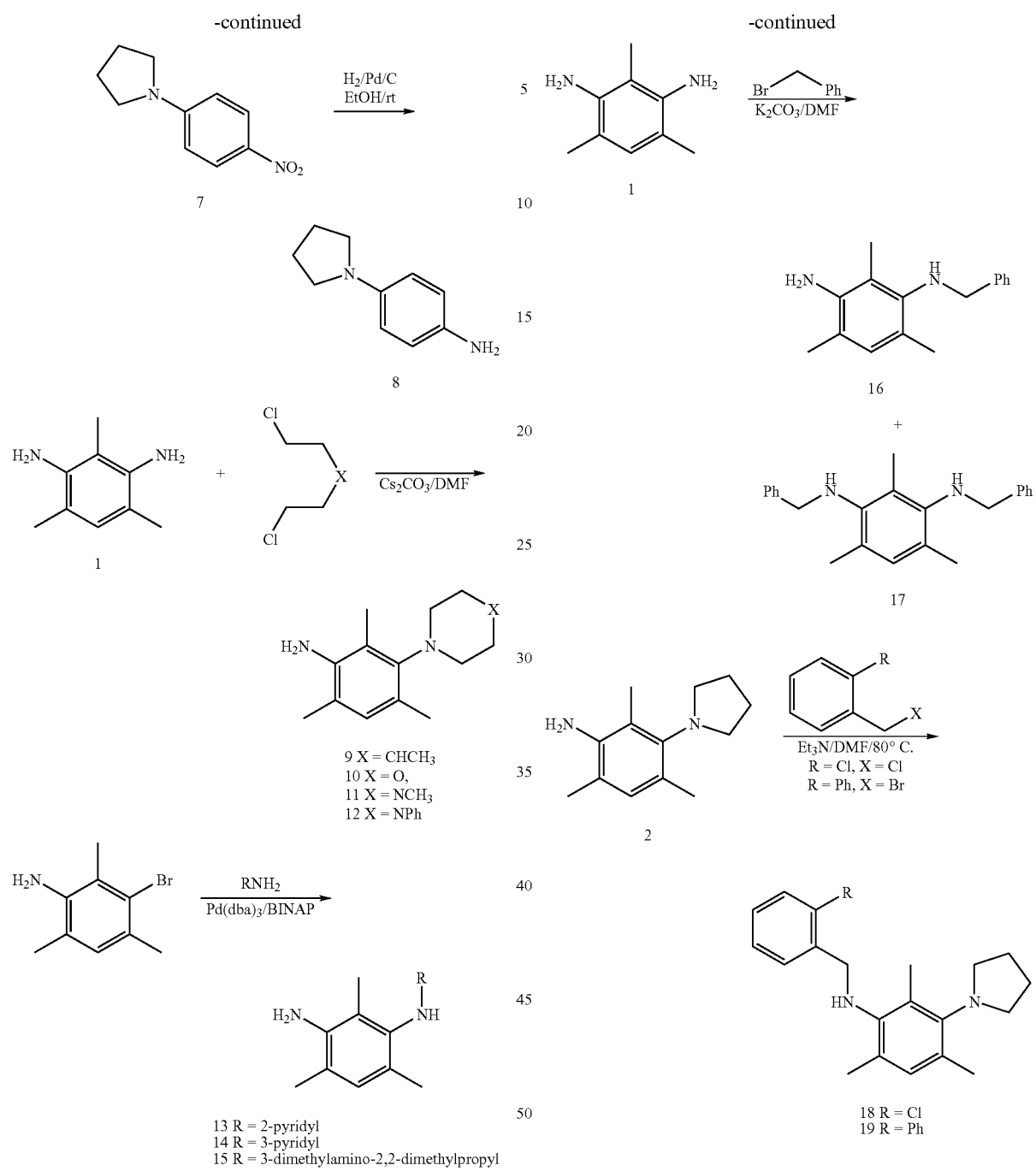
Scheme 2.
Synthesis of Amides and Sulfonamides
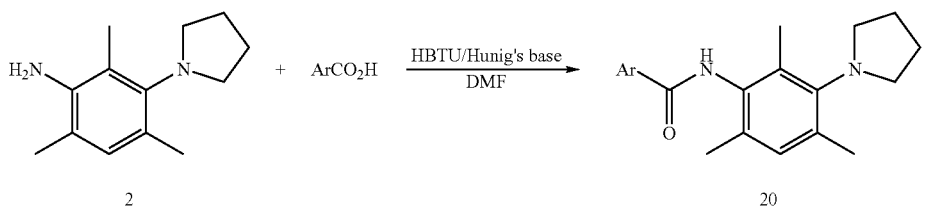

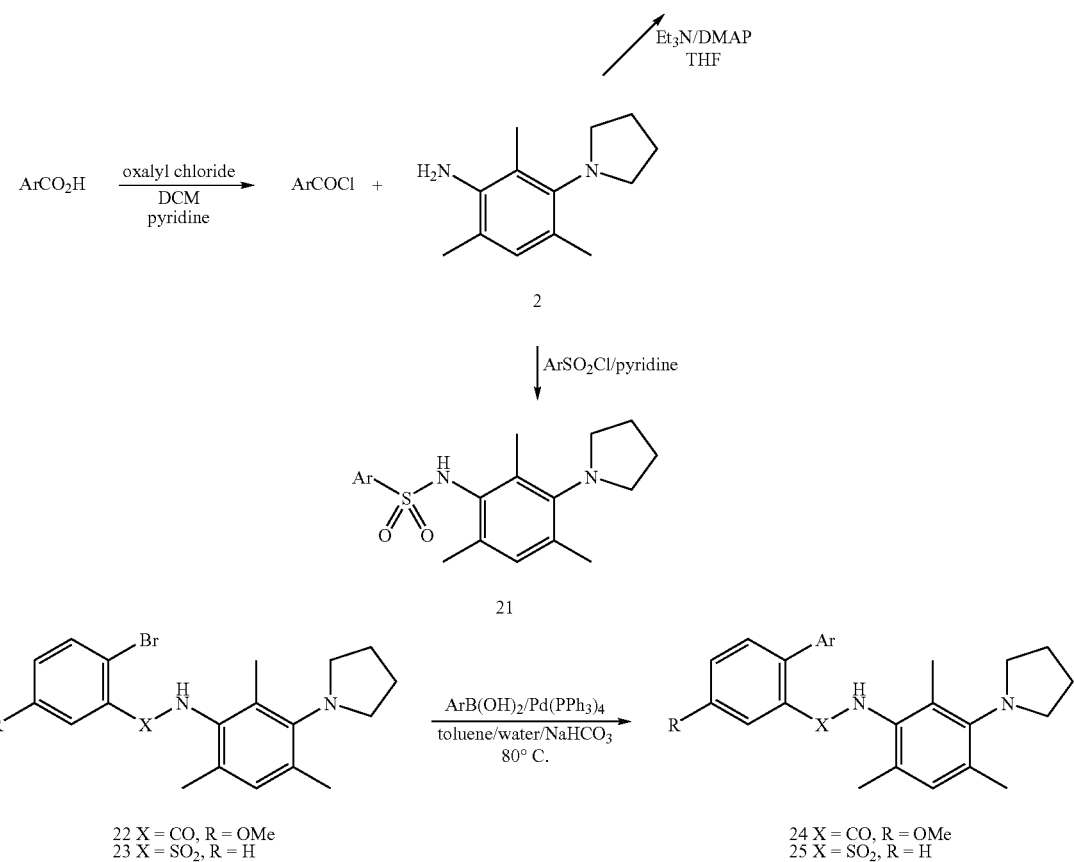
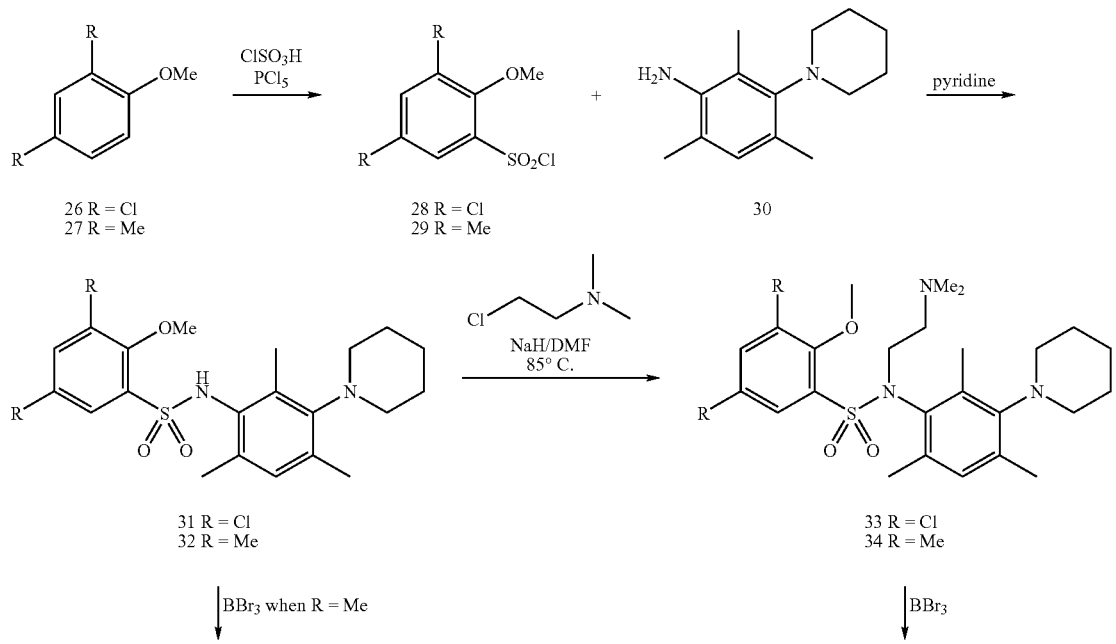
Scheme 3.
Synthesis of Sulfonamides

-continued
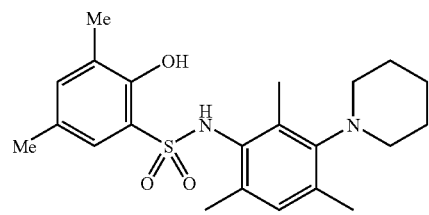
35
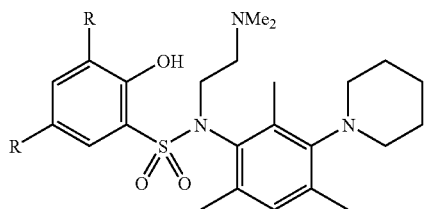
36 R = Cl
37 R = Me
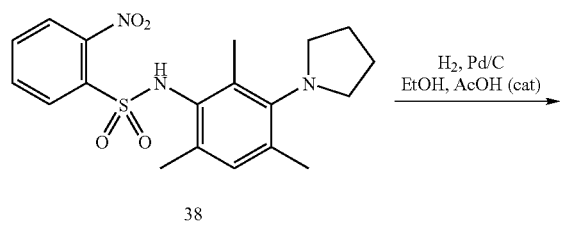
38
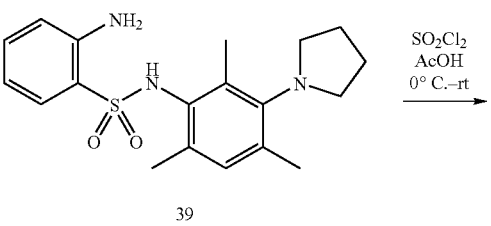
39
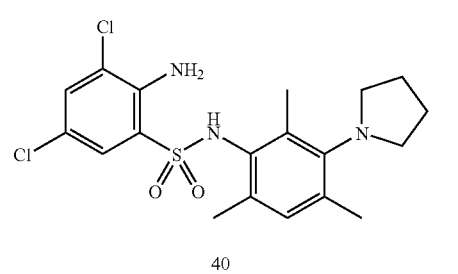
40
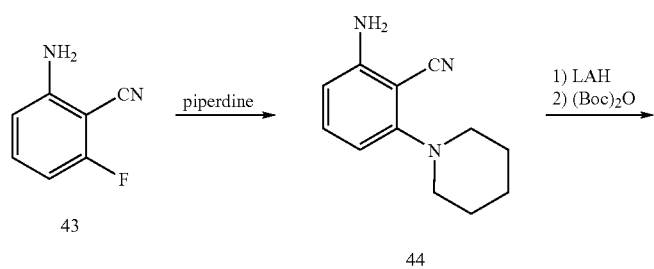
41 X = CO
42 X = SO$_2$
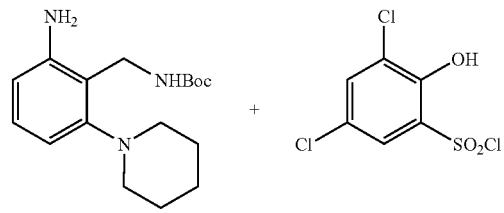
43 → 44
45 + 46
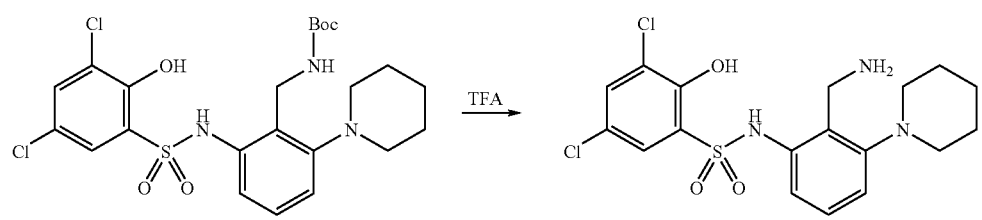
47 → 48

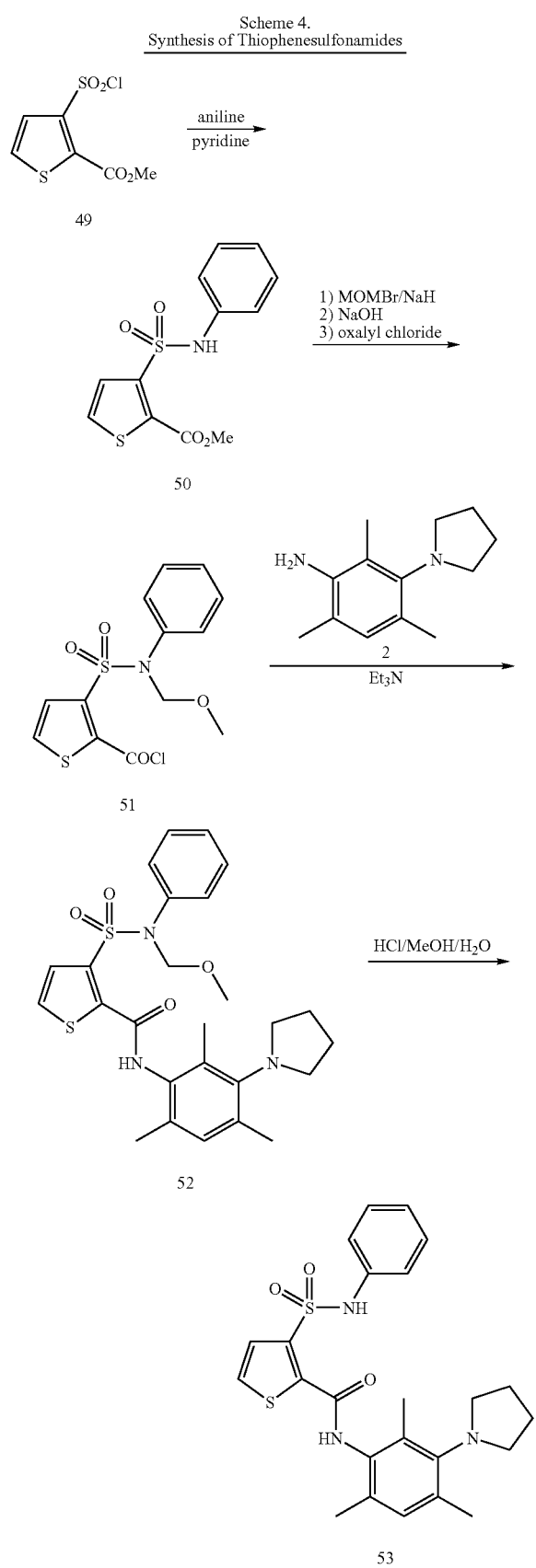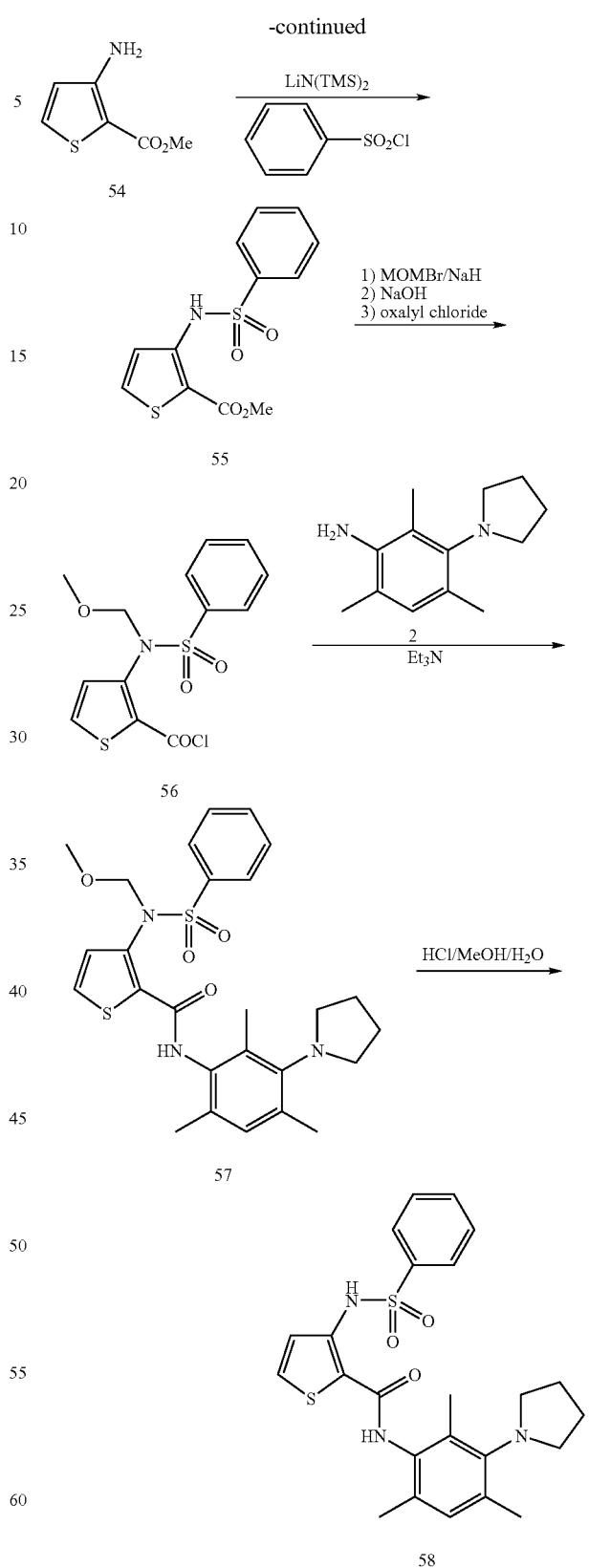
The compounds of the present invention can be used in the form of pharmaceutically acceptable salts derived from inorganic or organic acids. The phrase "pharmaceutically acceptable salt" means those salts which are, within the scope of soundmedical judgement, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in *J. Pharmaceutical Sciences*, 1977, 66:1 et seq. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, dighiconate, glycerophosphate, hemisulfate, heptanoate, hexanoate, fumarate, hydrochloride, hydrobromide, hydroiodide, 2-hydroxyethansulfonate (isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobtomic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylanmmonium, tetraethylammonium, methylainnonium, dimethylammonium, trimnethylammonium, triethylammonium, diethylammonium, and ethylammonium among others. Other representative organic amines useful for the formation of base addition salts include ethylenediamine, ethanolamine, diethanolamine, piperidine, piperazine and the like.

Dosage forms for topical administration of a compound of this invention include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the present invention can be employed in pure form or, where such forms exist, in pharmaceutically acceptable salt, ester or prodrug form. Alternatively, the compound can be administered as a pharmaceutical composition containing the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The present invention also provides pharmaceutical compositions that comprise compounds of the present invention formulated together with one or more non-toxic pharmaceutically acceptable carriers. The pharmaceutical compositions can be specially formulated for oral administration in solid or liquid form, for parenteral injection Or for rectal administration.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal,intrastemal, subcutaneous and intraarticular injection and infusion.

In another aspect, the present invention provides a pharmaceutical composition comprising a component of the present invention and a physiologically tolerable diluent. The present invention includes one or more compounds as described above formulated into compositions together with one or more non-toxic physiologically tolerable or acceptable diluents, carriers, adjuvants or vehicles that are collectively referred to herein as diluents, for parenteral injection, for intranasal delivery, for oral administration in solid or liquid form, for rectal or topical administration, among others.

The compositions can also be delivered through a catheter for local delivery at a target site, via an intracoronary stent (a tubular device composed of a fine wire mesh), or via a biodegradable polymer. The compounds may also be complexed to ligands, such as antibodies, for targeted delivery.

Compositions suitable for parenteral injection may comprise physiologically acceptable, sterile aqueous or non-aqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), vegetable oils (such as olive oil), injectable organic esters such as ethyl oleate, and suitable mixtures thereof These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid, b) binders such as carboxymethylcellulose, alginates, gelatin, polyvinylpyrrolidone, sucrose and acacia; c) hurnectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubillzing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof Besides inert diluents, the oral compositions may also include adjuvants such as wetting agents, emulsifying and suspending agents, sweetening, flavoring and perfuming agents.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes.

As is known in the art, liposomes are generally derived from phospholipids or other lipid substances. Liposomes are formed by mono- or multi-lamellar hydrated liquid crystals which are dispersed in an aqueous medium Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed, *Methods in Cell Biology*, Volume XIV, Academic Press, New York, N.Y. (1976), p. 33 et seq.

The term "pharmaceutically acceptable prodrugs" as used herein represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. Prodrugs of the present invention may be rapidly transformed in vivo to the parent compound of the above formula, for example, by hydrolysis in blood A thorough discussion is provided in T. Higuchi and V. Stella, *Pro-drugs as Novel Delivery Systems*, V. 14 of the A. C. S. Symposium Series, and in Edward B. Roche, ed., *Bioreversible Carriers in Drug Design*, American Pharmaceutical Association and Pergamon Press (1987), hereby incorporated by reference.

Compounds of the present invention that are formed by in vivo conversion of a different compound that was administered to a mammal are intended to be included within the scope of the present invention.

Compounds of the present invention may exist as stereoisomers wherein asymmetric or chiral centers are present. These stereoisomers are "R" or "S" depending on the configuration of substituents around the chiral carbon atom. The present invention contemplates various stereoisomers and mixtures thereof Stereoisomers include enantiomers and diastereomers, and mixtures of enantiomers or iastereomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiorners on chiral chromatographic columns.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

Preferably the composition is in unit dosage form, for example a tablet, capsule or metered aerosol dose, so that the patient may administer to th emselves a single dose.

Each dosage unit for oral administration contains suitably from 0.0001 mg to 500 mg/Kg, and preferably from 1 mg to 100 mg/Kg, and each dosage unit for parenteral administration contains suitably from 0.1 mg to 100 mg, of a compound of Formula (I) or a pharmaceutically acceptable salt thereof calculated as the free acid. Each dosage unit for intranasal administration contains suitably 1-400 mg and preferably 10 to 200 mg per person. A topical formulation contains suitably 0.01 to 1.0% of a compound of Formula (I).

The daily dosage regimen for oral administration is suitably about 0.01 mg/Kg to 40 mg/Kg, of a compound of Formula (I) or a pharmaceutically acceptable salt thereof calculated as the free acid. The daily dosage regimen for parenteral administration is suitably about 0.01 mg/Kg to 40 mg/Kg, of a compound of the Formula (I) or a pharmaceutically acceptable salt thereof calculated as the free acid. The daily dosage regimen for intranasal administration and oral inhalation is suitably about 10 to 500 mg/person. The active ingredient may be administered from 1 to 6 times a day, sufficient to exhibit the desired activity.

These compounds may be used for the treatment of congestive heart failure, stroke, ischemic heart disease (angina, myocardial ischemia), cardiac arrhythmia, hypertension (essential and pulmonary), renal disease (acute and chronic renal failure/end stage renal disease) along with peripheral vascular disease (male erectile dysfunction, diabetic retinopathy, intermittent claudication/ischemic limb disease) and ischemic/hemorrhagic stroke, COPD, restenosis, asthma, neurogenic inflammation, migraine, metabolic vasculopathies, bone/cartilage/joint disease, arthritis and other inflammatory diseases, fibrosis (e.g. pulmonary fibrosis), sepsis, atheroscloerosis, dyslipidemia, addiction, schizophrenia, cognitice disorders/Alzheimers disease, impulsivity, anxiety, stress, depression, pain, neuromuscular function, diabetes, gastric reflux, gastric motility disorders, ulcers and genitourinary diseases.

The urotension antagonist may be administered alone or in conjunction with one or more other therapeutic agents, said agents being selected from the group consisting of endothelin receptor antagonists, angiotensin converting enzyme (ACE) inhibitors, A-II receptor antagonists, vasopeptidase inhibitors, duuretics, digoxin, and dual non-selective $\beta$-adrenoceptor and $\alpha_1$-adrenoceptor antagonists.

The urotension related biological activity of the compounds of Formula (I) is demonstrated by the following tests:

1) Inhibition of Human [$^{125}$I]-Urotensin-II Binding to Urotensin-II Receptor Binding of human [$^{125}$I]-urotensin-II to human urotensin-II receptor (UTR) was done using cell membranes from either TE-671 rhabdomyosarcoma cells or CHO cells stably expressing recombinant UTR, in a homogeneous Scintillation Proximity Assay (SPA).

The UTR cells membranes were pre-coupled overnight at 4° C. to WGA-PVT beads (Amersham RPNQ0001) at a ratio of 5-25 µg membrane to 0.5 mg beads/assay. Assay was performed in 96-well microtiter Optiplates (Packard 6005290) by mixing coupled beads and 0.1 nM [$^{125}$I U-II (2200 Ci/mmol, NEN NEX379), in a total volume of 100 µl 20 mM HEPES, 5 mM MgCl$_2$, pH 7.4. Test compounds were diluted in DMSO and were put in the assay at a final concentration of 1% DMSO. Incubation was done for 3 hours at 37° C. followed by reading in a TopCount scintillation microplate reader. Nonspecific binding was determined by adding 100 nM unlabeled human U-II (Phoenix Pharmaceuticals, 071-05) to the assay mixture. Analysis of the assay was performed using nonlinear least square fitting.

1) Inhibition of Human Urotensin-II-induced Ca$^{2+}$ mobilization in UTR Cells:

The function of urotensin-II was determined by measuring ligand-induced mobilization of intracellular Ca$^{2+}$ in a FlexStation scanning fluorometer (Molecular Devices). UTR cells were plated overnight at 50,000 cells/well in 96-well black/clear plates (Costar brand, Fisher 07-200-588). Cells were labeled with fluo-4AM dye (Molecular Probes, F-14201) in Hank's balanced salt solution (HBSS), 20 mM HEPES, 25 mM probenecid, pH 7.4, and then were washed with buffer. During the assay, cells were continuously monitored in the FlexStation and exposed to test compounds at a final concentration of 0.1% DMSO, followed by the addition of 1 nM human U-II. Fluorescence was read every 2 seconds for 2 minutes. The excitation and emission wavelengths used were 485 run and 525 nm. Inhibition of the urotensin-II-induced signal was calculated using a nonlinear least square fitting program. Activity for the compounds of this invention is IC$_{50}$>0.5 mm (Example 30 IC$_{50}$=10 µM.

The CCR-9 antagonist activity of the compounds of the present invention is shown by the following assay:

CCR9 FLIPR/FlexStation Assay Protocol

Calcium assay in FLIPR/FlexStation determines inhibitors of TECK induced calcium mobilization in CCR9-Flp-CHO cells that stably over express human CCR-9 receptor. CCR-9-Flp-CHO cells are seeded at 20,000 cells/well in a clear bottom, black wall 96-well plate (Greiner) one day prior to assay. Cells are grown in a tissue culture incubator at 37° C. with 5% $CO_2$ for 18 to 24 hours.

Wash buffer and dye loading buffer are prepared fresh each time the assay is performed. Wash buffer is prepared according to the following protocol: 20 ml 10×HBSS, 4 ml 1 M HEPES, 176 ml sterile water, then add 142 mg Probenecid to solution and pH to 7.4. This wash buffer contains 1×HBSS, 20 mM HEPES and 2.5 mM probenecid. For one 96-well plate, dye loading buffer is prepared as following: 11 ml wash buffer, 44 □l Fluo-4/pluoronic acid mix (22 □l aliquot 2 mM Fluo-4 (Molecular Probes #F-14201, 50 μg/tube)+22 □l 20% pluronic F-127 (Molecular Devices, P-3000).

Cells are loaded with dye according to the protocol below:
1. Prepare wash buffer with 1×HBSS/HEPES at room temperature
2. Prepare loading buffer (keep in dark)
3. Aspirate culture media
4. Add 100 μl dye loading buffer to each well
5. Incubate at 37° C. for 1 hr
6. Aspirate loading buffer
7. Wash with 200 μl per well ×2
8. Add 100 μl wash buffer per well
9. Ready to assay plate with FLIPR or FlexStation 10 mM stock compounds in DMSO are prepared Compounds are diluted in wash buffer to make 8 point series dilutions containing same concentration of DMSO (less than 0.3%). Compounds are tested in duplicate wells for each point. Ligand rhTECK was diluted to 5× of its EC50 with wash buffer containing 0.5% BSA. Appropriate amount of 5× ligand is added to each well. Data is analyzed using GraphPad Prism software to calculate IC50 value of antagonist activity for each compound.

The following Examples are illustrative but not limiting of the present invention:

EXAMPLE 1

N-(2,4,6-trimethyl-3-pyrrolidin-1-yl-phenyl)-thiophene-2-carboxamide

1). 2,4,6-Trimethyl-3-pyrrolidin-1-yl-phenylamine (2). To a solution of 2,4,6-trimethyl-1,3-phenylenediamine (15.0 g, 99.8 mmol) in anhydrous DMF (300 mL) were sequentially added potassium carbonate (30.4 g, 219.7 mmol) and 1,4-dibromobutane (11.9 mL, 99.8 mmol). The reaction was stirred overnight and then partitioned between water and ethyl acetate. The organic layer was washed with brine, dried ($MgSO_4$) and concentrated. The residue was chromatographed eluting with hexanes:ethyl acetate (20:1) to give the desired product (10.8 g, 53%).

The titled compound was synthesized as shown in scheme 2 using 2 to give a white solid (ESI [M+H$^+$])=315.21.

Examples 2-97 (Table 1) were Synthesized in Similar Fashion.

| Example | structure | name | physical description | M + H |
|---|---|---|---|---|
| 1 | 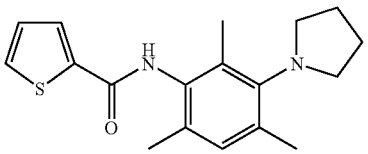 | N-(2,4,6-trimethyl-3-pyrrolidin-1-yl-phenyl)-thiophene-2-carboxamide | white solid | 315.21 |
| 2 | 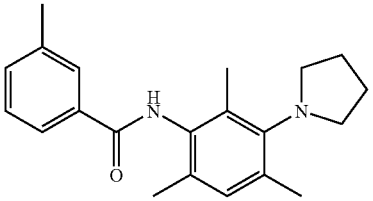 | 3-methyl-N-(2,4,6-trimethyl-3-pyrrolidin-1-yl-phenyl)-benzamide | yellow foam | 323.24 |
| 3 | 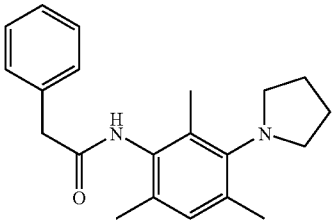 | 2-phenyl-N-(2,4,6-trimethyl-3-pyrrolidin-1-yl-phenyl)-acetamide | | 323.27 |

-continued

| Example | structure | name | physical description | M + H |
|---|---|---|---|---|
| 4 | 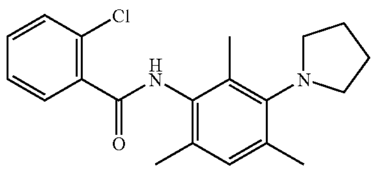 | 2-chloro-N-(2,4,6-trimethyl-3-pyrrolidin-1-yl-phenyl)-benzamide | yellow solid | 343.25 |
| 5 | 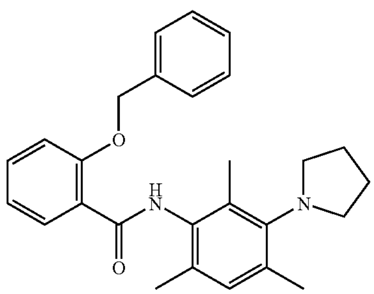 | 2-benzyloxy-N-(2,4,6-trimethyl-3-pyrrolidin-1-yl-phenyl)-benzamide | brown foam | 415.27 |
| 6 | 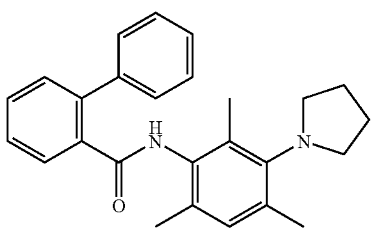 | N-(2,4,6-trimethyl-3-pyrrolidin-1-yl-phenyl)-biphenyl-2-carboxamide | yellow foam | 385.32 |
| 7 | 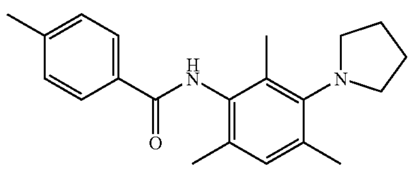 | 4-methyl-N-(2,4,6-trimethyl-3-pyrrolidin-1-yl-phenyl)-benzamide | light brown solid | 323.26 |
| 8 | 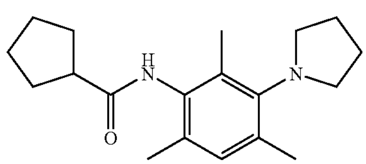 | N-(2,4,6-trimethyl-3-pyrrolidin-1-yl-phenyl)-cyclopentanecarboxamide | pale yellow solid | 301.25 |
| 9 | 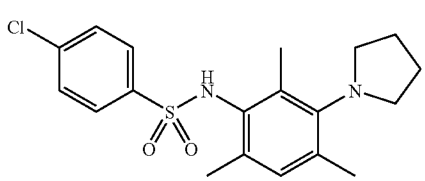 | 4-chloro-N-(2,4,6-trimethyl-3-pyrrolidin-1-yl-phenyl)-benzenesulfonamide | yellow solid | 379.12 |
| 10 | 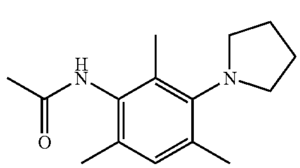 | N-(2,4,6-trimethyl-3-pyrrolidin-1-yl-phenyl)-acetamide | off-white solid | 247.26 |

| Example | structure | name | physical description | M + H |
|---|---|---|---|---|
| 11 | 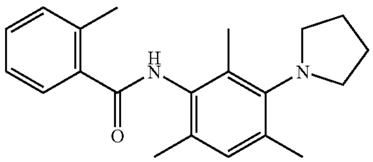 | 2-methyl-N-(2,4,6-trimethyl-3-pyrrolidin-1-yl-phenyl)-benzamide | off-white solid | 323.28 |
| 12 | 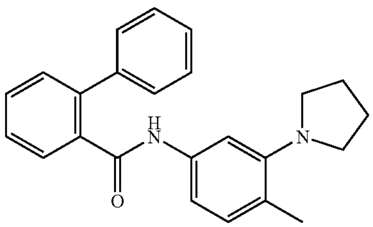 | N-(4-methyl-3-pyrrolidin-1-yl-phenyl)-biphenyl-2-carboxamide | dark tan solid | 357.29 |
| 13 | 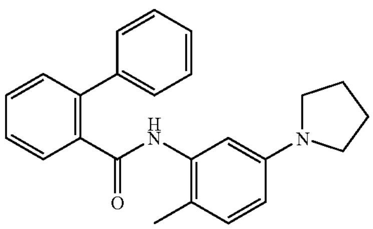 | N-(2-methyl-5-pyrrolidin-1-yl-phenyl)-biphenyl-2-carboxamide | white solid | 357.32 |
| 14 | 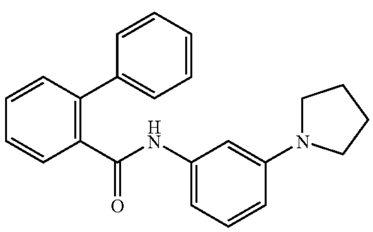 | N-(3-pyrrolidin-1-yl-phenyl)-biphenyl-2-carboxamide | yellow solid | 343.26 |
| 15 | 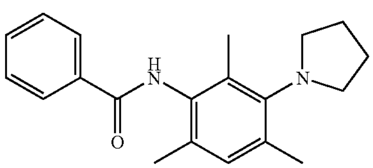 | N-(2,4,6-trimethyl-3-pyrrolidin-1-yl-phenyl)-benzamide | yellow solid | 309.23 |
| 16 | 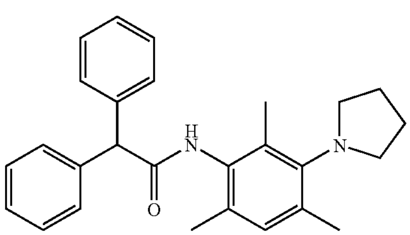 | 2,2-diphenyl-N-(2,4,6-trimethyl-3-pyrrolidin-1-yl-phenyl)-acetamide | white crystal | 399.28 |
| 17 | 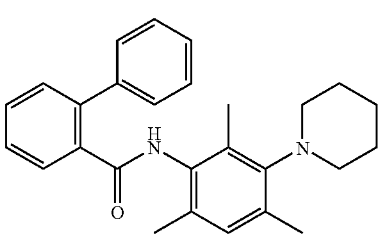 | N-(2,4,6-trimethyl-3-piperidin-1-yl-phenyl)-biphenyl-2-carboxamide | off-white solid | 399.28 |

-continued

| Example | structure | name | physical description | M + H |
|---|---|---|---|---|
| 18 | 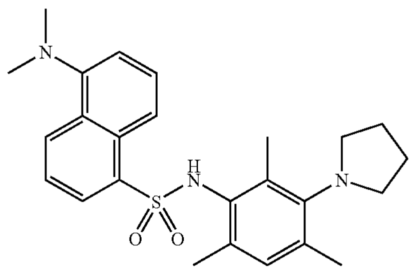 | 5-dimethylamino-N-(2,4,6-trimethyl-3-pyrrolidin-1-yl-phenyl)-naphthalene-1-sulfonamdie | light yellow foam | 438.24 |
| 19 | 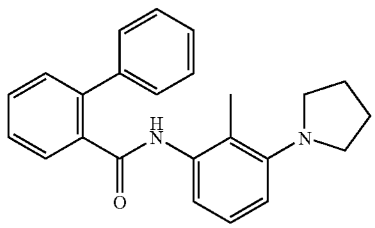 | N-(2-methyl-3-pyrrolidin-1-yl-phenyl)-biphenyl-2-carboxamide | white solid | 357.26 |
| 20 | 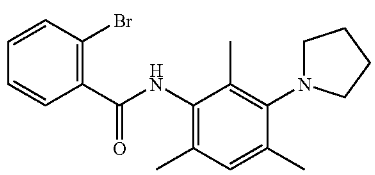 | 2-bromo-N-(2,4,6-trimethyl-3-pyrrolidin-1-yl-phenyl)-benzamide | white solid | 387.28 |
| 21 | 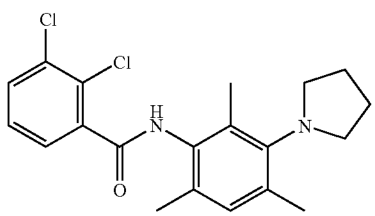 | 2,3-dichloro-N-(2,4,6-trimethyl-3-pyrrolidin-1-yl-phenyl)-benzamide | light yellow solid | 377.2 |
| 22 | 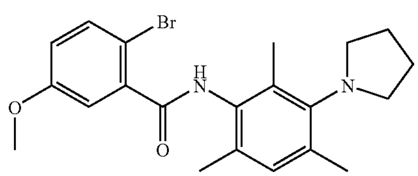 | 2-bromo-5-methoxy-N-(2,4,6-trimethyl-3-pyrrolidin-1-yl-phenyl)-benzamide | white solid | |
| 23 | 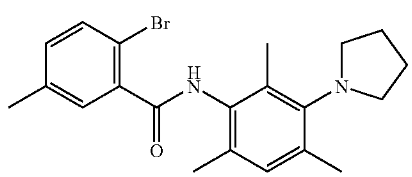 | 2-bromo-5-methyl-N-(2,4,6-trimethyl-3-pyrrolidin-1-yl-phenyl)-benzamide | yellow solid | |
| 24 | 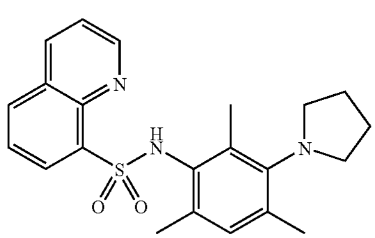 | N-(2,4,6-trimethyl-3-pyrrolidin-1-yl-phenyl)-quinoline-8-sulfonamide | light yellow foam | 396.17 |

| Example | structure | name | physical description | M + H |
|---|---|---|---|---|
| 25 | 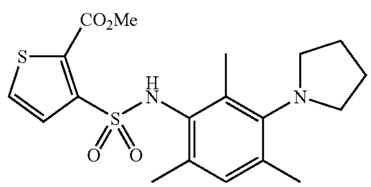 | methyl 3-(2,4,6-trimethyl-3-pyrrolidin-1-yl-phenylaminosulfonyl)-thiophene-2-carboxylate | yellowish solid | 409.17 |
| 26 | 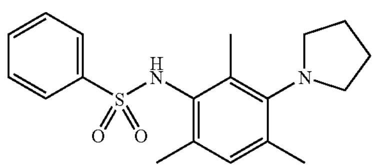 | N-(2,4,6-trimethyl-3-pyrrolidin-1-yl-phenyl)-benzenesulfonamide | white solid | 345.22 |
| 27 | 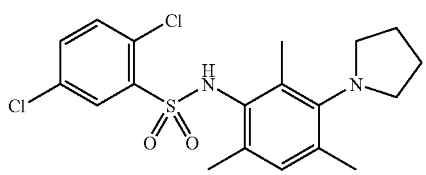 | 2,5-dichloro-N-(2,4,6-trimethyl-3-pyrrolidin-1-yl-phenyl)-benzenesulfonamide | white solid | 413.15 |
| 28 | 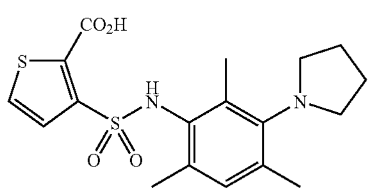 | 3-(2,4,6-trimethyl-3-pyrrolidin-1-yl-phenylaminosulfonyl)-thiophene-2-carboxylic acid | yellowish solid | 395.18 |
| 29 | 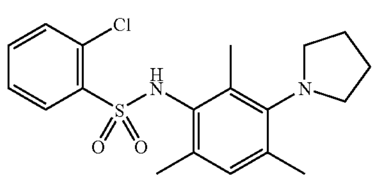 | 2-chloro-N-(2,4,6-trimethyl-3-pyrrolidin-1-yl-phenyl)-benzenesulfonamide | yellow solid | 379.14 |
| 30 | 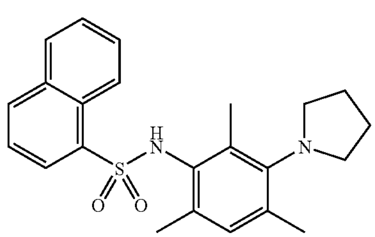 | N-(2,4,6-trimethyl-3-pyrrolidin-1-yl-phenyl)-naphthalene-1-sulfonamide | yellow solid | 395.25 |
| 31 | 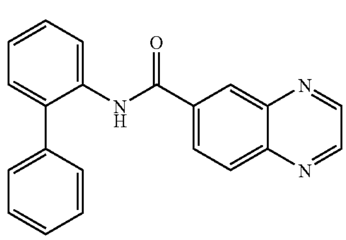 | N-(biphenyl-2-yl)-quinoxaline-6-carboxamide | yellow solid | 326.09 |

-continued

| Example | structure | name | physical description | M + H |
|---|---|---|---|---|
| 32 | 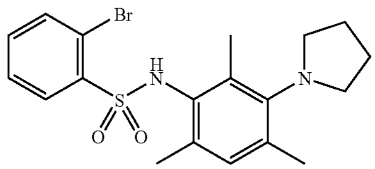 | 2-bromo-N-(2,4,6-trimethyl-3-pyrrolidin-1-yl-phenyl)-benzenesulfonamide | white solid | 423.14 |
| 33 | 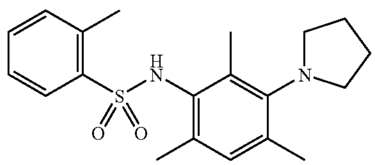 | 2-methyl-N-(2,4,6-trimethyl-3-pyrrolidin-1-yl-phenyl)-benzenesulfonamide | yellow solid | 359.17 |
| 34 | 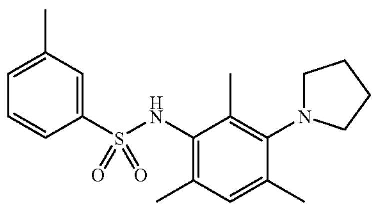 | 3-methyl-N-(2,4,6-trimethyl-3-pyrrolidin-1-yl-phenyl)-benzenesulfonamide | light yellow solid | 359.17 |
| 35 | 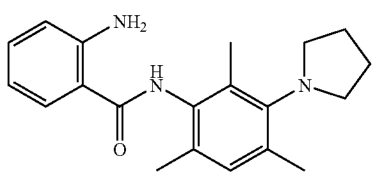 | 2-amino-N-(2,4,6-trimethyl-3-pyrrolidin-1-yl-phenyl)-benzamide | white solid | 324.28 |
| 36 | 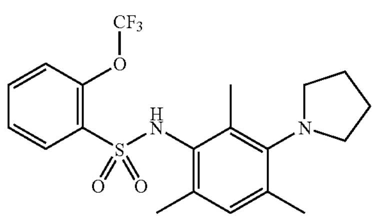 | 3-trifluoromethoxy-N-(2,4,6-trimethyl-3-pyrrolidin-1-yl-phenyl)-benzenesulfonamide | yellow solid | 427.13 M − H |
| 37 | 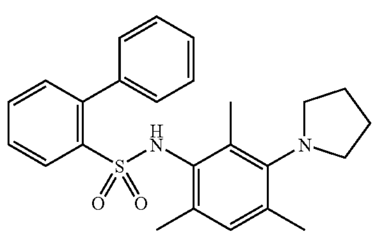 | N-(2,4,6-trimethyl-3-pyrrolidin-1-yl-phenyl)-biphenyl-2-sulfonamide | light yellow foam | 421.18 |
| 38 | 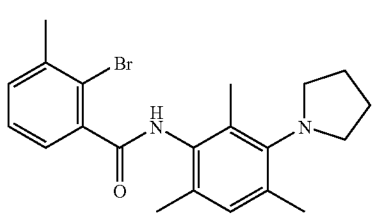 | 2-bromo-3-methyl-N-(2,4,6-trimethyl-3-pyrrolidin-1-yl-phenyl)-benzamide | colorless film | 401.1 |

| Example | structure | name | physical description | M + H |
|---|---|---|---|---|
| 39 | 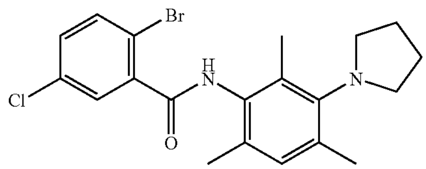 | 2-bromo-5-chloro-N-(2,4,6-trimethyl-3-pyrrolidin-1-yl-phenyl)-benzamide | white foam | 421.12 |
| 40 | 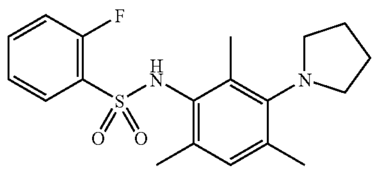 | 2-fluoro-N-(2,4,6-trimethyl-3-pyrrolidin-1-yl-phenyl)-benzenesulfonamide | yellow powder | 363.18 |
| 41 | 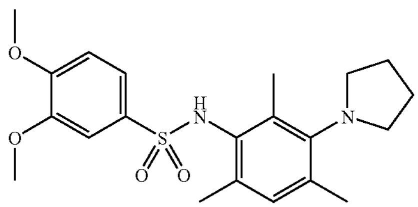 | 3,4-dimethoxy-N-(2,4,6-trimethyl-3-pyrrolidin-1-yl-phenyl)-benzenesulfonamide | tan solid | 405.27 |
| 42 | 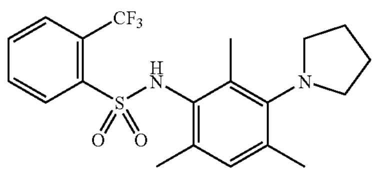 | 2-trifluoromethyl-N-(2,4,6-trimethyl-3-pyrrolidin-1-yl-phenyl)-benzenesulfonamide | low crystalline so | 423.11 |
| 43 | 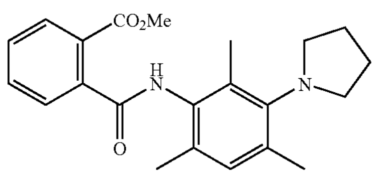 | methyl-N-(2,4,6-trimethyl-3-pyrrolidin-1-yl-phenyl)-phthalamate | white solid | 367.29 |
| 44 | 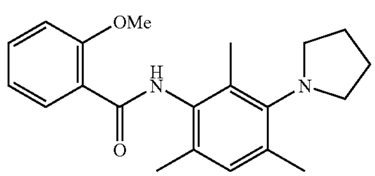 | 2-methoxy-N-(2,4,6-trimethyl-3-pyrrolidin-1-yl-phenyl)-benzamide | brown foam | 339.34 |
| 45 | 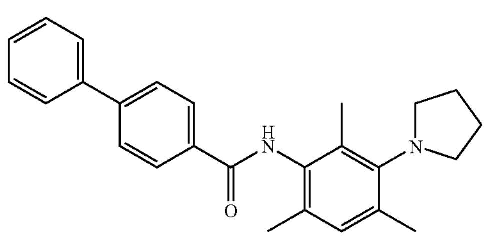 | N-(2,4,6-trimethyl-3-pyrrolidin-1-yl-phenyl)-biphenyl-4-carboxamide | white solid | 385.21 |
| 46 | 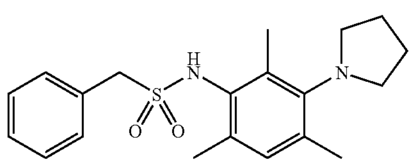 | N-(2,4,6-trimethyl-3-pyrrolidin-1-yl-phenyl)-phenylmethanesulfonamide | yellow foam | 359.23 |

-continued

| Example | structure | name | physical description | M + H |
|---|---|---|---|---|
| 47 | 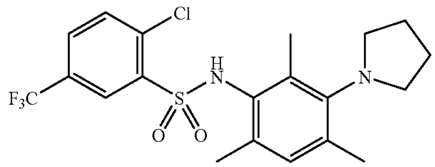 | 2-chloro-5-trifluoromethyl-N-(2,4,6-trimethyl-3-pyrrolidin-1-yl-phenyl)-benzenesulfonamide | tan solid | 447.19 |
| 48 | 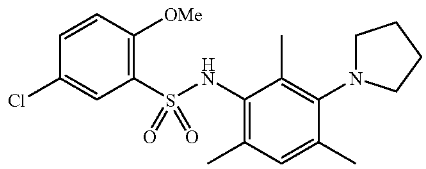 | 5-methoxy-2-chloro-N-(2,4,6-trimethyl-3-pyrrolidin-1-yl-phenyl)-benzenesulfonamide | | |
| 49 | 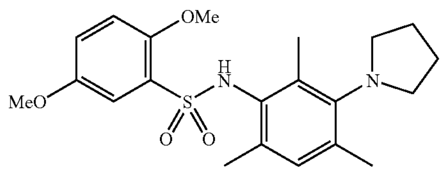 | 2,5-dimethoxy-N-(2,4,6-trimethyl-3-pyrrolidin-1-yl-phenyl)-benzenesulfonamide | oil | 405.27 |
| 50 | 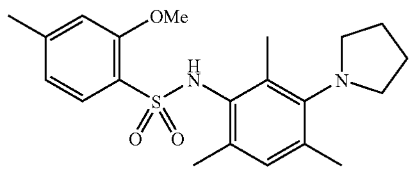 | 2-methoxy-4-methyl-N-(2,4,6-trimethyl-3-pyrrolidin-1-yl-phenyl)-benzenesulfonamide | light yellow foam | |
| 51 | 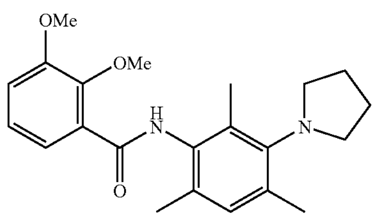 | 2,3-dimethoxy-N-(2,4,6-trimethyl-3-pyrrolidin-1-yl-phenyl)-benzamide | brown foam | 369.29 |
| 52 | 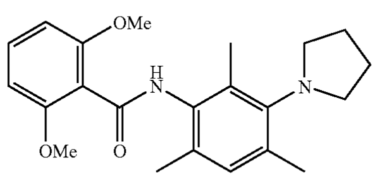 | 2,6-dimethoxy-N-(2,4,6-trimethyl-3-pyrrolidin-1-yl-phenyl)-benzamide | light brown solid | 369.29 |
| 53 | 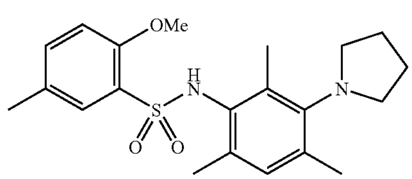 | 2-methoxy-5-methyl-N-(2,4,6-trimethyl-3-pyrrolidin-1-yl-phenyl)-benzenesulfonamide | light brown solid | 389.22 |
| 54 | 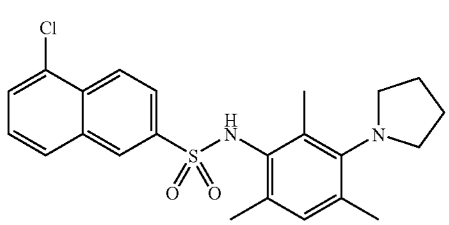 | 5-chloro-N-(2,4,6-trimethyl-3-pyrrolidin-1-yl-phenyl)-naphthalene-2-sulfonamide | tan solid | 429.22 |

-continued

| Example | structure | name | physical description | M + H |
|---|---|---|---|---|
| 55 | 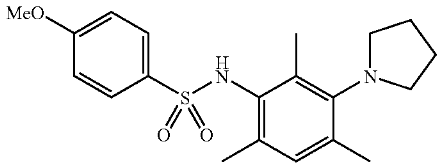 | 4-methoxy-N-(2,4,6-trimethyl-3-pyrrolidin-1-yl-phenyl)-benzenesulfonamide | white solid | 375.2 |
| 56 | 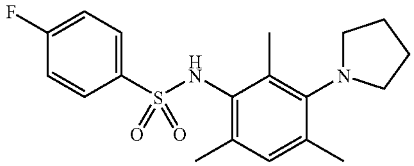 | 4-fluoro-N-(2,4,6-trimethyl-3-pyrrolidin-1-yl-phenyl)-benzenesulfonamide | | 363.14 |
| 57 | 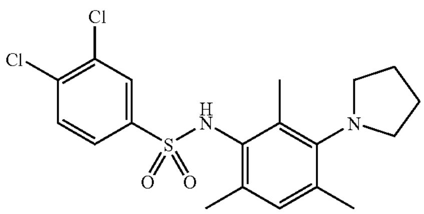 | 3,4-dichloro-N-(2,4,6-trimethyl-3-pyrrolidin-1-yl-phenyl)-benzenesulfonamide | light orange solid | 413.25 |
| 58 | 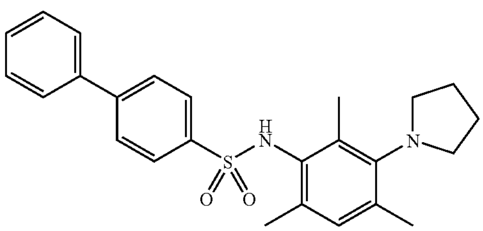 | N-(2,4,6-trimethyl-3-pyrrolidin-1-yl-phenyl)-biphenyl-4-sulfonamide | off-white solid | 421.23 |
| 59 | 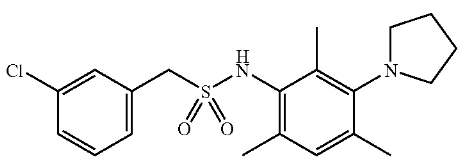 | C-(3-chlorophenyl)-N-(2,4,6-trimethyl-3-pyrrolidin-1-yl-phenyl)-methanesulfonamide | yellow foam | 393.18 |
| 60 | 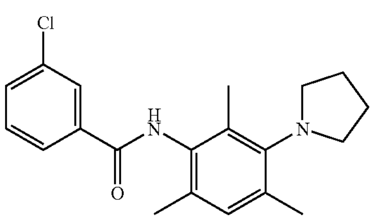 | 3-chloro-N-(2,4,6-trimethyl-3-pyrrolidin-1-yl-phenyl)-benzamide | yellow foam | 343.29 |
| 61 | 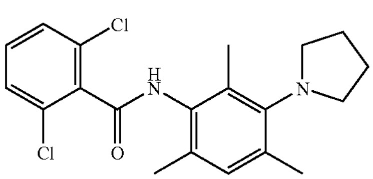 | 2,6-dichloro-N-(2,4,6-trimethyl-3-pyrrolidin-1-yl-phenyl)-benzamide | brown solid | 377.14 |
| 62 | 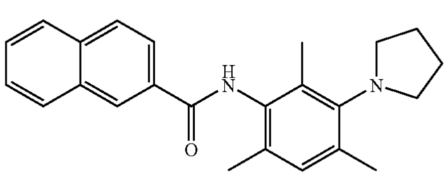 | N-(2,4,6-trimethyl-3-pyrrolidin-1-yl-phenyl)-naphthalene-2-carboxamide | off-white solid | 359.26 |

-continued

| Example | structure | name | physical description | M + H |
|---|---|---|---|---|
| 63 | 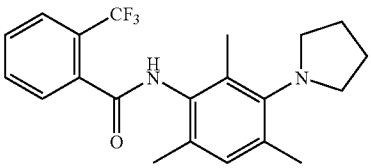 | 2-trifluoromethyl-N-(2,4,6-trimethyl-3-pyrrolidin-1-yl-phenyl)-benzamide | yellow solid | 377.21 |
| 64 | 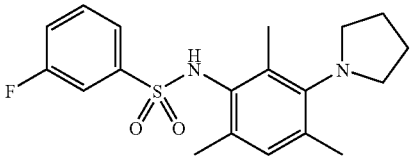 | 3-fluoro-N-(2,4,6-trimethyl-3-pyrrolidin-1-yl-phenyl)-benzenesulfonamide | yellow solid | 363.07 |
| 65 | 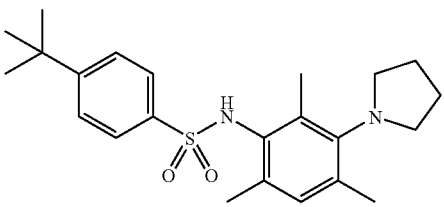 | 4-tert-butyl-N-(2,4,6-trimethyl-3-pyrrolidin-1-yl-phenyl)-benzenesulfonamide | tan crystals | 401.25 |
| 66 | 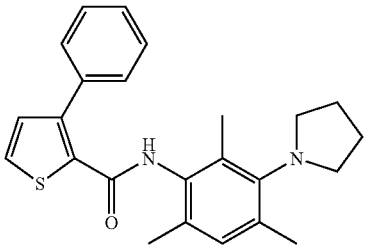 | 3-phenyl-N-(2,4,6-trimethyl-3-pyrrolidin-1-yl-phenyl)-thiophene-2-carboxamide | brown solid | 391.16 |
| 67 | 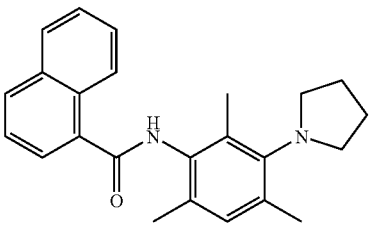 | N-(2,4,6-trimethyl-3-pyrrolidin-1-yl-phenyl)-naphthalene-1-carboxamide | off-white foam | 359.27 |
| 68 | 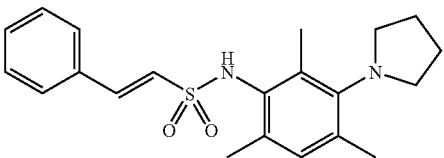 | 2-phenyl-N-(2,4,6-trimethyl-3-pyrrolidin-1-yl-phenyl)-ethenesulfonamide | light yellow foam | |
| 69 | 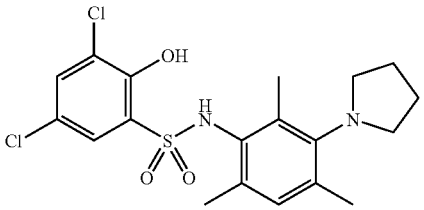 | 3,5-dichloro-2-hydroxy-N-(2,4,6-trimethyl-3-pyrrolidin-1-yl-phenyl)-benzenesulfonamide | off-white solid | 429.12 |

-continued

| Example | structure | name | physical description | M + H |
|---|---|---|---|---|
| 70 | 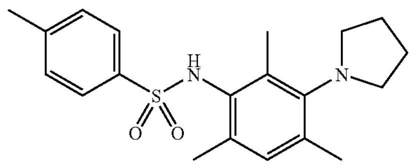 | 4-methyl-N-(2,4,6-trimethyl-3-pyrrolidin-1-yl-phenyl)-benzenesulfonamide | light brown solid | 359.11 |
| 71 | 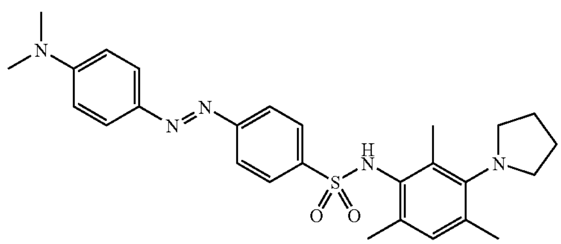 | 4-(4-dimethylamino-phenylazo)-N-(2,4,6-trimethyl-3-pyrrolidin-1-yl-phenyl)-benzenesulfonamide | | 492.15 |
| 72 | 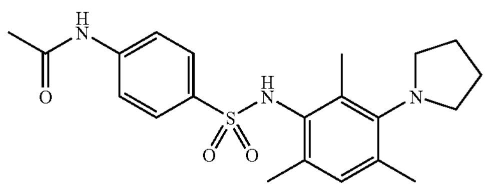 | N-(4-(2,4,6-trimethyl-3-pyrrolidin-1-yl-phenyl)aminosulfonyl)-phenyl-acetamide | | 402.15 |
| 73 | 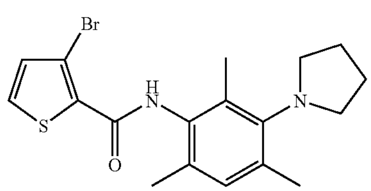 | 3-bromo-N-(2,4,6-trimethyl-3-pyrrolidin-1-yl-phenyl)-thiophene-2-carboxamide | yellowish solid | 393.07 |
| 74 | 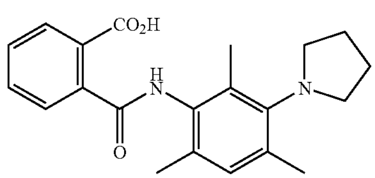 | N-(2,4,6-trimethyl-3-pyrrolidin-1-yl-phenyl)-phthalamic acid | yellowish solid | 353.14 |
| 75 | 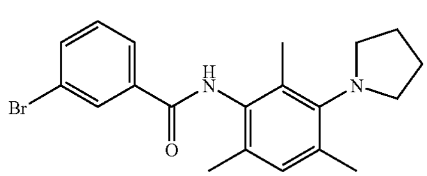 | 3-bromo-N-(2,4,6-trimethyl-3-pyrrolidin-1-yl-phenyl)-benzamide | white solid | 387.21 |
| 76 | 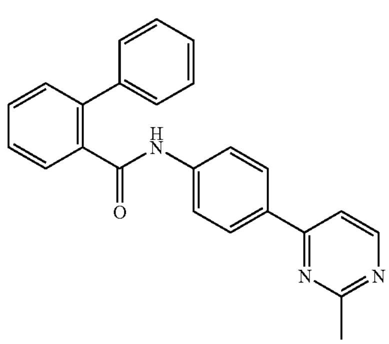 | N-(4-(2-methyl-pyrimidin-4-yl)-phenyl)-biphenyl-2-carboxamide | | |

-continued

| Example | structure | name | physical description | M + H |
|---|---|---|---|---|
| 77 | 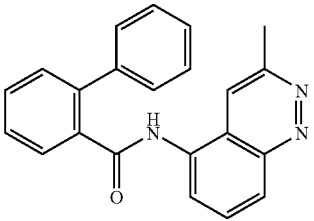 | N-(3-methyl-cinnolin-5-yl)-biphenyl-2-carboxamide | | |
| 78 | 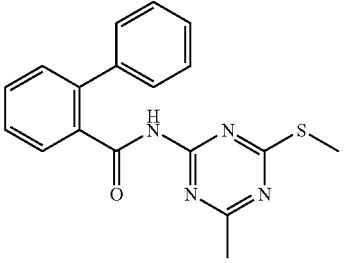 | N-(4-methyl-6-methylthio-(1,3,5)-triazin-2-yl)-biphenyl-2-carboxamide | | |
| 79 | 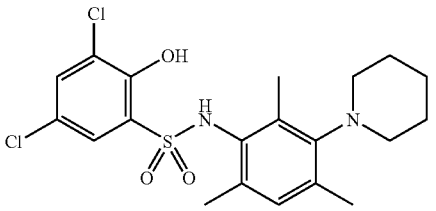 | 3,5-dichloro-2-hydroxy-N-(2,4,6-trimethyl-3-(piperidin-1-yl)-phenyl)-benzenesulfonamide | light yellow foam | 442.99 |
| 80 | 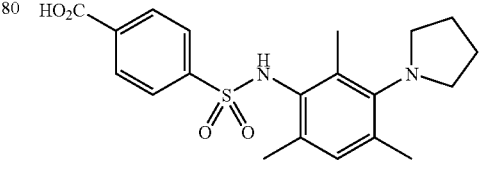 | 4-((2,4,6-trimethyl-3-pyrrolidin-1-yl-phenyl)-aminosulfonyl)-benzoic acid | pale yellow solid | 389.09 |
| 81 | 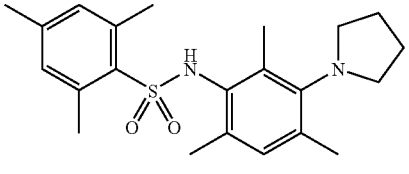 | 2,4,6-trimethyl-N-(2,4,6-trimethyl-3-pyrrolidin-1-yl-phenyl)-benzenesulfonamide | off-white solid | 387.22 |
| 82 | 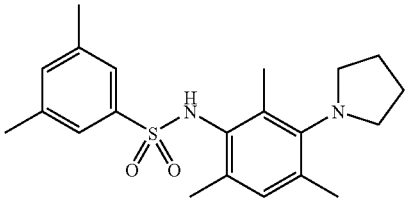 | 3,5-dimethyl-N-(2,4,6-trimethyl-3-pyrrolidin-1-yl-phenyl)-benzenesulfonamide | light orange solid | 373.24 |

-continued

| Example | structure | name | physical description | M + H |
|---|---|---|---|---|
| 83 | 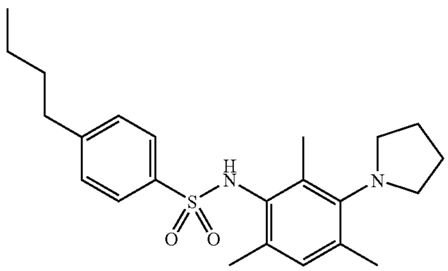 | 4-butyl-N-(2,4,6-trimethyl-3-pyrrolidin-1-yl-phenyl)-benzenesulfonamide | tan solid | 401.21 |
| 84 | 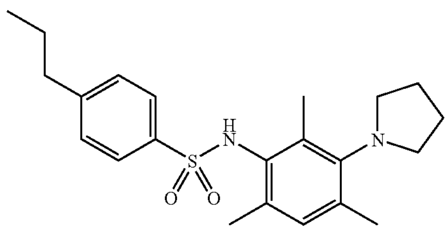 | 4-propyl-N-(2,4,6-trimethyl-3-pyrrolidin-1-yl-phenyl)-benzenesulfonamide | tan solid | 387.21 |
| 85 | 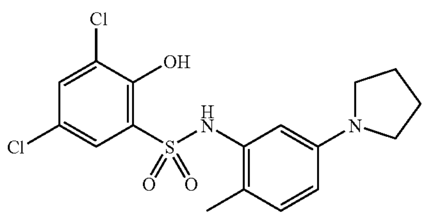 | 3,5-dichloro-2-hydroxy-N-(2-methyl-5-pyrrolidin-1-yl-phenyl)-benzenesulfonamide | yellow solid | 401.15 |
| 86 | 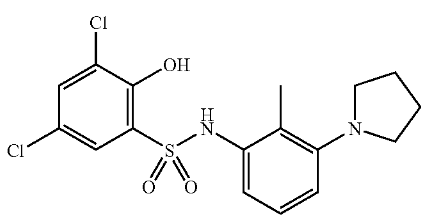 | 3,5-dichloro-2-hydroxy-N-(2-methyl-3-pyrrolidin-1-yl-phenyl)-benzenesulfonamide | light pink solid | 401.14 |
| 87 | 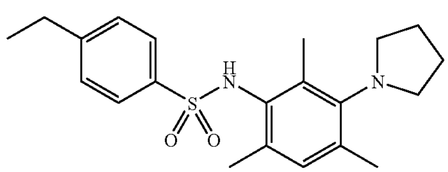 | 4-ethyl-N-(2,4,6-trimethyl-3-pyrrolidin-1-yl-phenyl)-benzenesulfonamide | off-white solid | 373.13 |
| 88 | 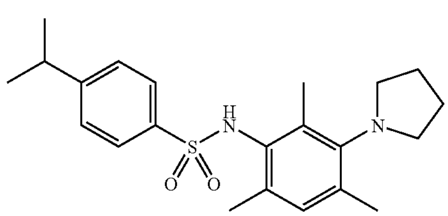 | 4-isopropyl-N-(2,4,6-trimethyl-3-pyrrolidin-1-yl-phenyl)-benzenesulfonamide | pale orange solid | 387.21 |
| 89 | 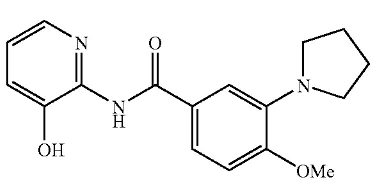 | N-(3-hydroxy-pyridin-2-yl)-4-methoxy-3-pyrrolidin-1-yl-benzamide | beige solid | 314.36 |

-continued

| Example | structure | name | physical description | M + H |
|---|---|---|---|---|
| 90 | 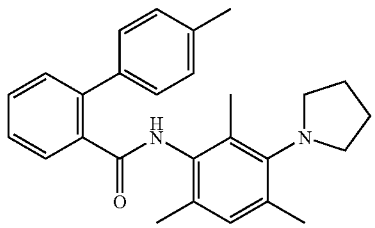 | 4'-methyl-N-(2,4,6-trimethyl-3-pyrrolidin-1-yl-phenyl)-biphenyl-2-carboxamide | yellow solid | |
| 91 | 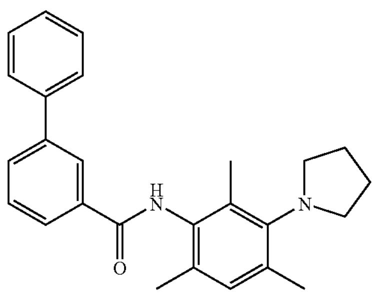 | N-(2,4,6-trimethyl-3-pyrrolidin-1-yl-phenyl)-biphenyl-3-carboxamide | colorless oil | |
| 92 | 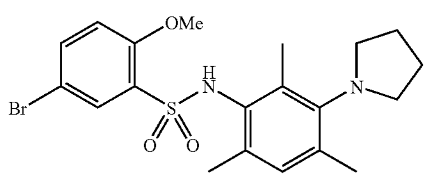 | 5-bromo-2-methoxy-N-(2,4,6-trimethyl-3-pyrrolidin-1-yl-phenyl)-benzenesulfonamide | white solid | |
| 93 | 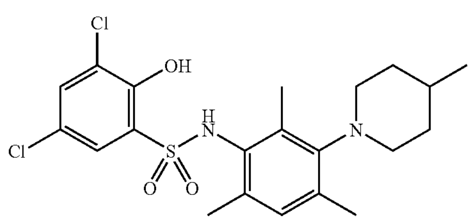 | 3,5-dichloro-2-hydroxy-N-(2,4,6-trimethyl-3-(4-methylpiperidin-1-yl)-phenyl)-benzenesulfonamide | yellow solid | 457.04 |
| 94 | 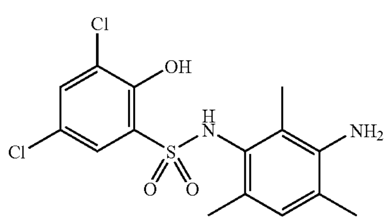 | 3,5-dichloro-2-hydroxy-N-(3-amino-2,4,6-trimethyl-phenyl)-benzenesulfonamide | tan solid | 375.04 |
| 95 | 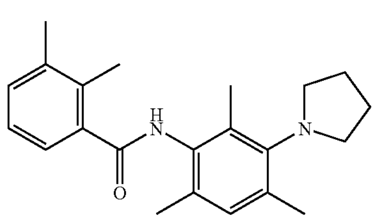 | 2,3-dimethyl-N-(2,4,6-trimethyl-3-pyrrolidin-1-yl-phenyl)-benzamide | white foam | 337.28 |

-continued

| Example | structure | name | physical description | M + H |
|---|---|---|---|---|
| 96 | 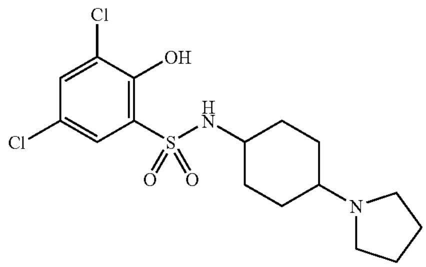 | 3,5-dichloro-2-hydroxy-N-(4-pyrrolidin-1-yl-cyclohexyl)-benzenesulfonamide | white solid | 379.17 |
| 97 | 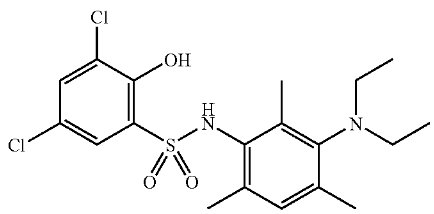 | 3,5-dichloro-N-(3-diethylamino-2,4,6-trimethyl-phenyl)-2-hydroxy-benzenesulfonamide | yellow solid | 431.2 |

EXAMPLE 97

3,5-dichloro-N-(3-diethylamino-2,4,6-trimethyl-phenyl)-2-hydroxy-benzenesulfonamide 1) Diethylamino-2,4,6-trimethyl-phenylamine (5). Compound 5 was synthesized as shown in Scheme 1 using a literature procedure (Wu, et. al. *J Med. Chem.* 1999, 42, 4485-4499).

2) The title compound was synthesized by coupling of 5 with 3,5-dichloro-2-hydroxybenzenesulfonyl chloride as shown in Scheme 2 for 21 to give a yellow solid (ESI [M+H$^+$]=431.2).

EXAMPLE 98

3,5-dichloro-2-hydroxy-N-(4-pyrrolidin-1-yl-phenyl)-benzenesulfonamide 1) 1-(4-Nitrophenyl)-pyrrolidine (7). To a solution of 4-nitroaniline (1 g, 7.2 mmol) in DMF (20 mL) was added sodium hydride (60% in mineral oil, 0.579 g, 14.4 mmol). The mixture was placed under nitrogen atmosphere and stirred for 5 minutes before the addition of 1,4-Dibromobutane (0.86 mL, 7.2 mmol). The resulting mixture was stirred for additional 15 min and then extracted with ethyl acetate (30 mL, 20 mL) and washed with water and brine (15 mL each). The ethyl acetate extracts were combined and dried (MgSO$_4$), the solids filtered and the filtrate concentrated to give the crude 7 as a yellow solid.

2) 4-(Pyrrolidin-1-yl)-phenylamine (8). To a solution of 7 in ethanol (20 mL) was added 10 wt % Pd on carbon (Degussa) (25 mg, 23 □mol). Glacial acetic acid (2-3 drops) was added to the reaction. The reaction was placed under a H$_2$ atmosphere and stirred for 16 hours, after which the reaction mixture was filtered through a pad of celite. The filtrate was evaporated, and the residue then dissolved in ethyl acetate (20 mL) and washed with 2N HCl (aq. 15 mL). The aqueous phase was isolated and then basified by the addition of 2N NaOH (aq. 20 mL). The aqueous layer was extracted with ethyl acetate (20 mL×2). The ethyl acetate extracts were dried over anhydrous magnesium sulfate, filtered, and evaporated to give crude 8 as a yellow oil (642 mg, 55% for 2 steps).

3) The title compound was synthesized in the same fashion as for 21 (Scheme 2) using 8 and 3,5-dichloro-2-hydroxybenzenesulfonyl chloride as a yellow solid (ESI M+H=387.18).

EXAMPLE 119

4-Chloro-N-(2,4,6-trimethyl-3-(4-methyl-piperizin-1-yl)-phenyl)-benzenesulfonamide 1). 2,4,6-Trimethyl-3-(4-methyl-piperizin-1-yl)-phenylamine (11). To a solution of 1 (1.5 g, 10 mmol) in anhydrous DMF (20 mL) were sequentially added mechlorethamine hydrochloride (1.93 g, 10 mmol) and cesium carbonate (10.4 g, 32 mmol). The resulting mixture was heated for 6 hours at 120° C. under nitrogen and was worked up as usual. Column chromatography eluting with EtOAc:methanol (10:1) then 100% methanol gave 900 mg of 11.

2) The title compound was synthesized following the protocol shown in Scheme 2 using 11 and 4-chlorobenzenesulfonyl chloride as a yellow solid (ESI M+H=408.21). The compounds of Examples 99-118 and 120-128 are prepared by the procedures of Examples 98 and 119.

| | | | | |
|---|---|---|---|---|
| 98 | 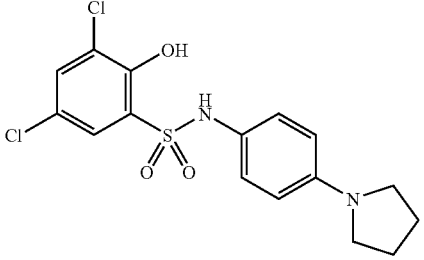 | 3,5-dichloro-2-hydroxy-N-(4-pyrrolidin-1-yl-phenyl)-benzenesulfonamide | yellow solid | 387.18 |
| 99 | 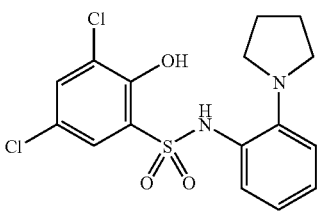 | 3,5-dichloro-2-hydroxy-N-(2-pyrrolidin-1-yl-phenyl)-benzenesulfonamide | brown solid | 387.13 |
| 100 | 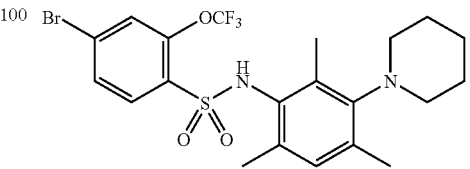 | 4-bromo-2-trifluoromethyl-N-(2,4,6-trimethyl-3-piperidin-1-yl-phenyl)-benzenesulfonamide | white solid | 521.15 |
| 101 | 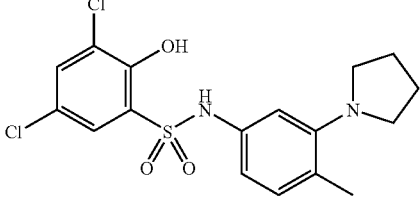 | 3,5-dichloro-2-hydroxy-N-(4-methyl-3-pyrrolidin-1-yl-phenyl)-benzenesulfonamide | light brown solid | 401.08 |
| 102 | 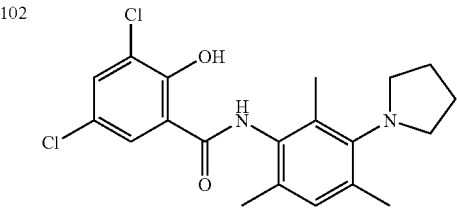 | 3,5-dichloro-2-hydroxy-N-(2,4,6-trimethyl-3-pyrrolidin-1-yl-phenyl)-benzamide | light brown foam | 393.14 |
| 103 | 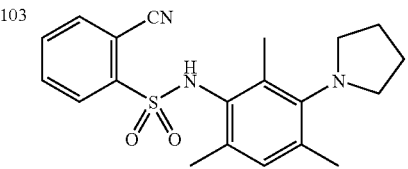 | 2-cyano-N-(2,4,6-trimethyl-3-pyrroiidin-1-yl-phenyl)-benzenesulfonamide | brownish solid | 370.05 |
| 104 | 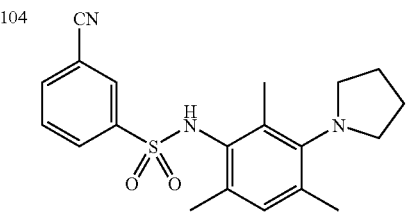 | 3-cyano-N-(2,4,6-trimethyl-3-pyrrolidin-1-yl-phenyl)-benzenesulfonamide | brownish solid | 370.19 |

-continued

| | | | | |
|---|---|---|---|---|
| 105 | [structure] | 4-cyano-N-(2,4,6-trimethyl-3-pyrrolidin-1-yl-phenyl)-benzenesulfonamide | yellowish solid | 370.17 |
| 106 | [structure] | 3,5-dichloro-2-hydroxy-N-(3,4-dimethyl-3-pyrrolidin-1-yl-phenyl)-benzenesulfonamide | pink solid | 415.10 |
| 107 | [structure] | 3,5-dichloro-2-hydroxy-N-(4,5-dimethyl-2-pyrrolidin-1-yl-phenyl)-benzenesulfonamide | | 415.05 |
| 108 | [structure] | 3,5-dichloro-2-hydroxy-N-(3,5-dimethyl-3-pyrrolidin-1-yl-phenyl)-benzenesulfonamide | orange solid | 415.17 |
| 109 | [structure] | N-benzyl-3,5-dichloro-N-(2-dimethylamino-ethyl)-2-hydroxy-benzenesulfonamide | white solid | 403.17 |
| 110 | [structure] | 3,5-dichloro-N-(2-cyano-3-piperidin-1-yl-phenyl)-2-hydroxy-benzenesulfonamide | off-white solid | 423.97 |
| 111 | [structure] | 3,5-dichloro-N-(3-(1,3-dihydro-isoindol-2-yl)-2,4,6-trimethyl-phenyl)-2-hydroxy-benzenesulfonamide | tan solid | |

-continued

| Example | Structure | name | physical description | M + H |
|---|---|---|---|---|
| 112 | 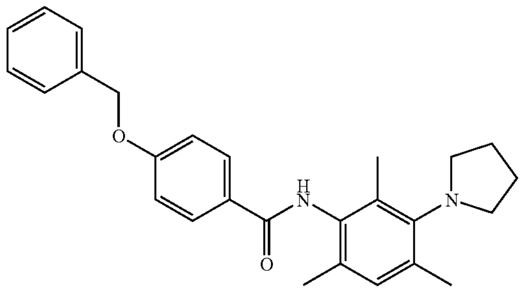 | 4-benzyloxy-N-(2,4,6-trimethyl-3-pyrrolidin-1-yl-phenyl)-benzamide | white solid | |
| 113 | 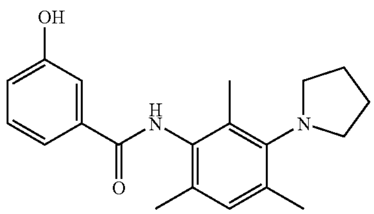 | 3-hydroxy-N-(2,4,6-trimethyl-3-pyrrolidin-1-yl-phenyl)-benzamide | yellow solid | |
| 114 | 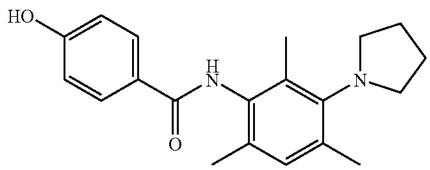 | 4-hydroxy-N-(2,4,6-trimethyl-3-pyrrolidin-1-yl-phenyl)-benzamide | yellow solid | |
| 115 | 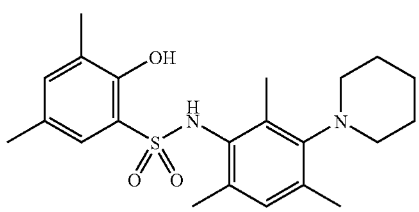 | 2-hydroxy-3,5-dimethyl-N-(2,4,6-trimethyl-3-piperlidin-1-yl-phenyl)-benzenesulfonamide | brownish solid | 402.24 |
| 116 | 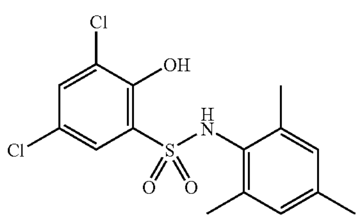 | 3,5-dichloro-2-hydroxy-N-(2,4,6-trimethylphenyl)-benzenesulfonamide | light yellow foam | 358.17 M − H |

| Example | Structure | name | physical description | M + H |
|---|---|---|---|---|
| 117 | | N-(2,4,6-trimethyl-3-morpholin-4-yl-phenyl)-biphenyl-2-carboxamide | off-white solid | 401.26 |
| 118 | | 4-chloro-N-(2,4,6-trimethyl-3-morpholin-4-yl-phenyl)- | brownish solid | 395.14 |

-continued

| | | | | |
|---|---|---|---|---|
| 119 | | 4-chloro-N-(2,4,6-trimethyl-3-(4-methyl-piperizin-1-yl)-phenyl)-benzenesulfonamide | yellow solid | 408.21 |
| 120 | | N-(2,4,6-trimethyl-3-(4-methyl-piperizin-1-yl)-phenyl)-biphenyl-2-carboxamide | yellowish solid | 414.36 |
| 121 | | 3-methyl-N-(2,4,6-trimethyl-3-(4-phenyl-piperizin-1-yl)-phenyl)-benzenesulfonamide | off-white solid | 450.25 |
| 122 | | 4-tert-butyl-N-(2,4,6-trimethyl-3-(4-methyl-piperizin-1-yl)-phenyl)-benzenesulfonamide | brownish solid | 429.18 |
| 123 | | 3-chloro-N-(2,4,6-trimethyl-3-(4-methyl-piperizin-1-yl)-phenyl)-benzamide | white solid | 371.16 |
| 124 | | 4-tert-butyl-N-(2,4,6-trimethyl-3-(4-phenyl-piperizin-1-yl)-phenyl)-benzenesulfonamide | white solid | 492.26 |
| 125 | | 3,5-dichloro-2-hydroxy-N-(2,4,6-trimethyl-3-(4-phenyl-piperizin-1-yl)-phenyl)-benzenesulfonamide | yellowish solid | 520.06 |

-continued

| | | | |
|---|---|---|---|
| 126 | [structure] | 3,5-dichloro-2-hydroxy-N-(2,4,6-trimethyl-3-morpholin-4-yl-phenyl)-benzenesulfonamide | pink foam |
| 127 | [structure] | 3,5-dichloro-2-hydroxy-N-(2,4,6-trimethyl-3-(4-methylpiperidin-1-yl)-phenyl)-benzenesulfonamide | yellow solid 457.04 |
| 128 | [structure] | 3,5-dichloro-2-hydroxy-N-(2,4,6-trimethyl-3-(4-methylpiperizin-1-yl)-phenyl)-benzenesulfonamide | yellow solid 458.1 |

EXAMPLE 129

4-tert-Butyl-N-(3-(3-dimethylamino-2,2-dimethyl-propylamino)-2,4,6-trimethyl-phenyl)-benzene-sulfonamide 1)N-(3-Dimethylamino-2,2-dimethyl-propyl)-2,4,6-trimnethyl-benzene-1,3-diamine (15)

Sodium tert-butoxide (288.33 mg, 3 mmol), $Pd_2(dba)_3$, (104 mg, 0.1 mmol), and BINAP (125 mg, 0.2 mmol) were mixed in a sealed tube and the tube was purged with $N_2$. 3-Bromo-2,4,6-trimethyl-aniline (428.22 mg, 2 mmol) and 2,2-$N^1$,$N^1$-tetramethyl-propane-1,3-diamine (0.413 ml, 2.6 mmol) and toluene (5 mL) were then sequentially added to the tube. The mixture was degassed three times and filled with $N_2$, sealed, and heated for 36 hours at 100° C. The tube was cooled to room temperature and worked up as usual. The crude products were purified by loaded into column chromatography (florisil) eluting with hexanes: EtOAc (3:1 to 1:2 ratio) to give 329 mg 15.

2). The titled compound was synthesized as shown in Scheme 2 using 15 and 4-tert-butylbenzenesulfonyl chloride as a yellow solid (ESI [M+H$^+$]=460.11).

The compounds of Examples 130-132 are prepared by the procedure of Example 129.

| Example | Structure | name | physical description | M + H |
|---|---|---|---|---|
| 130 | [structure] | 3,5-dichloro-2-hydroxy-N-(3-(3-dimethylamino-2,2-dimethylpropylamino)-2,4,6-trimethyl-phenyl)-benzenesulfonamide | yellowish solid | 488.21 |
| 131 | [structure] | 3,5-dichloro-2-hydroxy-N-(2,4,6-trimethyl-3-(pyridin-3-ylamino)-phenyl)-benzenesulfonamide | white solid | 452.07 |

| Example | Structure | name | physical description | M + H |
|---|---|---|---|---|
| 132 | 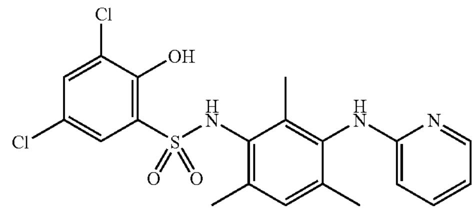 | 3,5-dichloro-2-hydroxy-N-(2,4,6-trimethyl-3-(pyridin-3-ylamino)-phenyl)-benzenesulfonamide | yellowish solid | 452.12 |

EXAMPLE 133 AND 134

N-(3-Benzylamino-2,4,6-trimethyl-phenyl)-3,5-dichloro-2-hydroxy-benzenesulfonamide and N-benzyl-N-(3-benzylamino-2,4,6-trimethyl-phenyl)-3,5-dichloro-2-hydroxy-benzenesulfonamide 1) N-Benzyl-2,4,6-trimethyl-benzene-1,3-diamine (16) and N,N'-dibenzyl-2,4,6-trimethyl-benzene-1,3-diamine (17)

To a solution of 2,4,6-trimethyl-1,3-phenylenediamine (2.0 g, 13.3 mmol) in anhydrous DMF (40 mL) were sequentially added potassium carbonate (2.8 g, 20.0 mmol) and benzyl bromide (1.6 mL, 13.3 mmol). The reaction was stirred overnight and partitioned between water and ethyl acetate. The organic layer was washed with brine, dried (MgSO₄), the solids were filtered off and the filtrate concentrated The residue was chromatographed eluting with hexanes:ethyl acetate (80:1-40:1-20:1) to give a 1:1 mixture of 16 and 17.

2). The title compounds were synthesized as shown in Scheme 2 using 3,5-dichloro-2-hydroxy-benzenesulfonyl chloride and 16, 17, respectively, as white foams. ESI [M+H⁺]=465.04 (example 133); M−H=553.075 for (example 134).

EXAMPLE 135

(2-chloro-benzyl)-(2,4,6-trimethyl-3-pyrrolidin-1-yl-phenyl)-amine 18

To a solution of aniline 1 (121 mg, 0.59 mmol) in DMF (4.9 mL) was added triethylamine (0.141 mL, 1.00 mmol). 2-Chlorobenzyl chloride (0.08 mL, 0.63 mmol) was then added, and the reaction was heated at 80° C. for 22 hrs. After cooling the reaction mixture to room temperature, the mixture was extracted with ethyl acetate (20 mL×2) and washed with water and brine (10 mL each). The ethyl acetate extracts were dried over anhydrous magnesium sulfate, filtered, and evaporated to give the crude product. Column chromatography on silica (15:1 to 7:1 hexanes/ethyl acetate) gave the product ($R_f$=0.6 in 10/1 hexanes/ethyl acetate) as a yellow oil (14 mg, 7%). ESI [M+H⁺]=329.1.

EXAMPLE 136

Biphenyl-2-ylmethyl-(2,4,6-trimethyl-3-pyrrolidin-1-yl-phenyl)-amine (19)

The title compound was synthesized in the same manner as for example 135 as a yellow oil. ESI [M+H⁺]=371.19.

EXAMPLE 137

4-Methoxy-N-(2,4,6-trimethyl-3-pyrrolidin-1-yl-phenyl)-biphenyl-2-carboxamide

To a solution of the aryl bromide 22 (example 22) (106 mg, 0.25 mmol) in toluene (2.4 mL) was added saturated aqueous sodium bicarbonate solution (1.0 ml). The mixture was placed under a nitrogen atmosphere followed by the addition of a solution of phenyl boronic acid (43 mg, 0.35 mmol) in EtOH (1.8 mL). Pd(Ph₃P)₄ (19 mg, 0.02 mmol) was added, and the reaction was then heated at 80° C. for 70 hrs. After cooling the reaction mixture to room temperature, the mixture was extracted with ethyl acetate (30 mL, 20 mL) and washed with water and brine (15 mL each). The ethyl acetate extracts were dried over anhydrous magnesium sulfate, filtered, and evaporated to give the crude product. Column chromatography on silica (5:1 to 4:1 hexanes/ethyl acetate) gave the product ($R_f$=0.4 in 3/1 hexanes/ethyl acetate) as a white solid (46 mg, 44%). ESI [M+H⁺]=415.21.

The compounds of Examples 138-148 are prepared by the procedure of Example 137.

| Example | Structure | name | physical description | M + H |
|---|---|---|---|---|
| 137 | 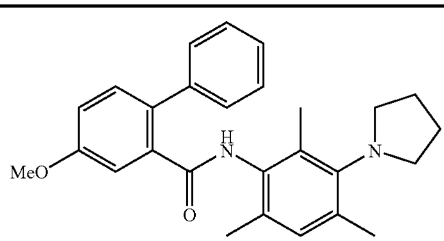 | 4-methoxy-N-(2,4,6-trimethyl-3-pyrrolidin-1-yl-phenyl)-biphenyl-2-carboxamide | white solid | 415.21 |

-continued

| Example | Structure | name | physical description | M + H |
|---|---|---|---|---|
| 138 | 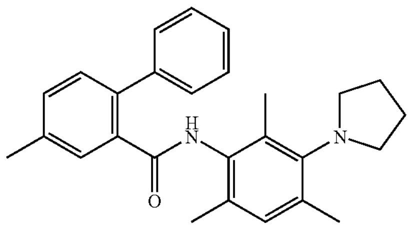 | 4-methyl-N-(2,4,6-trimethyl-3-pyrrolidin-1-yl-phenyl)-biphenyl-2-carboxamide | white solid | 399.24 |
| 139 | 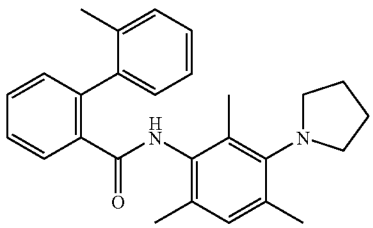 | 2'-methyl-N-(2,4,6-trimethyl-3-pyrrolidin-1-yl-phenyl)-biphenyl-2-carboxamide | yellow solid | |
| 140 | 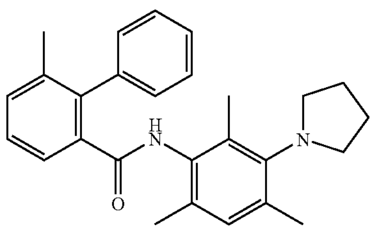 | 6-methyl-N-(2,4,6-trimethyl-3-pyrrolidin-1-yl-phenyl)-biphenyl-2-carboxamide | white solid | 299.26 |
| 141 | 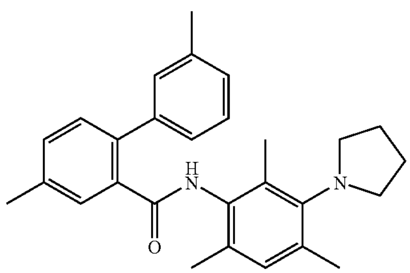 | 3'-methyl-N-(2,4,6-trimethyl-3-pyrrolidin-1-yl-phenyl)-biphenyl-2-carboxamide | yellow solid | 399.29 |
| 142 | 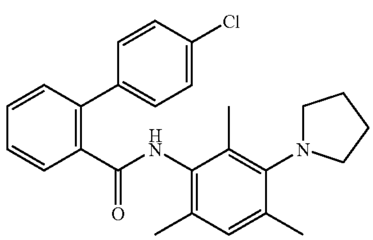 | 4'-chloro-N-(2,4,6-trimethyl-3-pyrrolidin-1-yl-phenyl)-biphenyl-2-carboxamide | white solid | 419.2 |
| 143 | 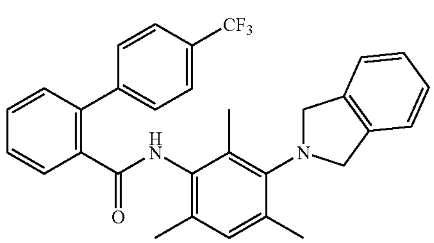 | 4-trifluoromethyl-N-(2,4,6-trimethyl-3-(1,3-dihydro-isoindol-2-yl)-phenyl)-biphenyl-2-carboxamide | yellow solid | 501.25 |

| Example | Structure | name | physical description | M + H |
|---|---|---|---|---|
| 144 | 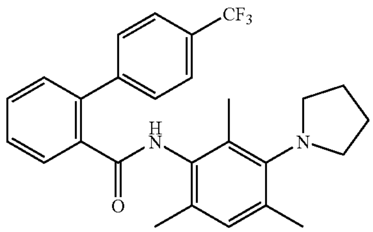 | N-(2,4,6-trimethyl-3-pyrrolidin-1-yl-phenyl)-biphenyl-2-carboxamide | white solid | 453.19 |
| 145 | 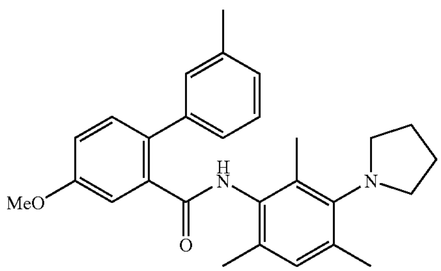 | 4-methoxy-3'-methyl-N-(2,4,6-trimethyl-3-pyrrolidin-1-yl-phenyl)-biphenyl-2-carboxamide | yellow solid | |
| 146 | 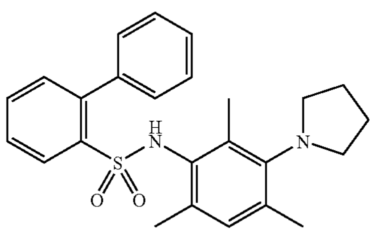 | N-(2,4,6-trimethyl-3-pyrrolidin-1-yl-phenyl)-biphenyl-2-sulfonamide | light yellow foam | 421.18 |
| 147 | 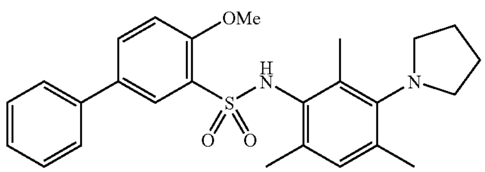 | 4-methoxy-N-(2,4,6-trimethyl-3-pyrrolidin-1-yl-phenyl)-biphenyl-3-sulfonamide | white solid | 451.21 |
| 148 | 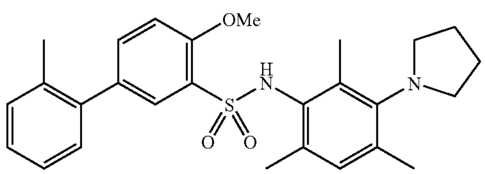 | 4-methoxy-2'-methyl-N-(2,4,6-trimethyl-3-pyrrolidin-1-yl-phenyl)-biphenyl-3-sulfonamide | yellow oil/gel | 465.25 |

EXAMPLE 149

2-Phenyl-N-(2,4,6-trimethyl-3-pyrrolidin-1-yl-phenyl)-ethanesulfonamide

To a solution of Example 68 (0.20 g, 0.55 mmol) in EtOH (8 mL) was added Pd (10% on carbon, degussa, 0.20 g) and 10 drops of AcOH. This mixture was then sealed with a septum and put under vacuum for 1 minute before subjected to a H$_2$ atmosphere overnight at room temperature. TLC indicated the reaction did not go to completion. After filtration to remove the catalyst, the filtrate was concentrated and the desired product was separated by silica gel chromatography (10% to 25% EtOAc in hexanes) to yield 0.070 g of the title compound as a yellow solid. ESI [M+H$^+$]= 373.16.

EXAMPLE 150

2-Methoxy-3,5-dimethyl-N-(2,4,6-trimethyl-3-piperidin-1-yl-phenyl)-benzenesulfonamide (32)

1) 2-Methoxy-3,5-dimethyl-benzenesulfonyl chloride (29). To a solution of 2,4-dimethylanisole (4.18 g, 30 mmol) in anhydrous 1,2-dichloroethane (45 mL) at 0° C. and under N$_2$ were added dropwise ClSO$_3$H (2.55 mL, 38 mmol) and PCl$_5$ (6.7 g, 31.5 mmol) in portions. The mixture was stirred overnight at room temperature and poured into ice water with vigorous stirring. The aqueous mixture was extracted with dichloromethane and the organic layer was washed with brine two times and dried over NaSO$_4$. The solids were filtered off and the filtrate was concentrated in a rotavap to afford 29 (4.5 g).

2) The title compounds was synthesized as usual (Scheme 2) using 29 and the phenylenediamine 30 as a white solid ESI [M+H$^+$]=417.22.

EXAMPLE 151

(TBC6274). 3,5-Dichloro-2-methoxy-N-(2,4,6-trimethyl-3-piperidin-1-yl-phenyl)-benzenesulfonamide (31)

The title compound was synthesized in the same manner as for example 150 as a light yellow foam.

EXAMPLE 152

N-(2-(Dimethylamino)-ethyl)-2-methoxy-3,5-dimethyl-N-(2,4,6-trimethyl-3-piperidin-1-yl-phenyl)-benzenesulfonamide (34)

To a solution of 32 (103 mg, 0.25 mmol) in anhydrous DMF (5 mL) was added NaH (60% dispersion in mineral oil, 22 mg, 0.54 mmol). The mixture was stirred for 10 min at room temperature before the addition of 2-(dimethylamino)-ethyl chloride hydrochloride (39.2 mg, 0.27 mmol). The resulting mixture was heated overnight at 85° C. After a usual workup, the residue was loaded onto column (Florisil) and the column eluted with EtOAc/CH$_3$OH (10:1) to give 80 mg of the title compound as an off-white solid ESI [M+H$^+$]=488.27.

EXAMPLE 153

3,5-Dichloro-N-(2-(dimethylamino)-ethyl)-2-methoxy-N-(2,4,6-trimethyl-3-piperidin-1-yl-phenyl)-benzenesulfonamide (33)

The title compound was synthesized in the same manner as for Example 152 as light yellow foam. ESI [M+H$^+$]= 528.28.

EXAMPLE 154

2-Hydroxy-3,5-dimethyl-N-(2,4,6-trimethyl-3-piperidin-1-yl-phenyl)-benzenesulfonamide (35)

Under a nitrogen atomersphere, 32 (88 mg, 0.21 mmol) was dissolved in dichloromethane (6 mL) followed by the addition of BBr$_3$ (0.2 mL, 2.1 mmol). The reaction was stirred overnight at room temperature and then quenched with ice. The mixture was partitioned between EtOAc and water and the organic layer was separated, washed with brine, and dried over Na$_2$SO$_4$. The solids were filtered off and the filtrate was concentrated in a rotavap to give 70 mg of the title compound as a brownish solid ESI [M+H$^+$]=402.24.

The compounds of Examples 155-160 are prepared by the procedure of Example 154.

| Example | structure | name | physical description | M + H |
|---|---|---|---|---|
| 154 | 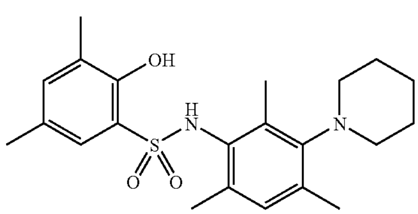 | 2-hydroxy-3,5-dimethyl-N-(2,4,6-trimethyl-3-piperidin-1-yl-phenyl)-benzenesulfonamide | brownish solid | 402.24 |
| 155 | 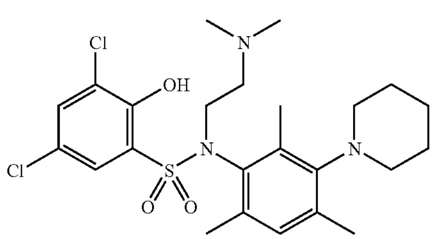 | 3,5-dichloro-N-(2-(dimethylamino)-ethyl)-2-hydroxy-N-(2,4,6-trimethyl-3-piperidin-1-yl-phenyl)-benzenesulfonamide | yellow solid | 514.25 |
| 156 | 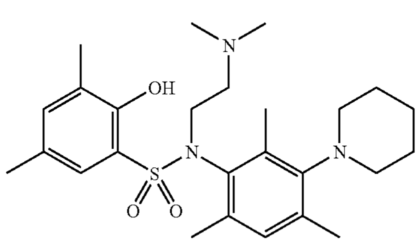 | N-(2-(dimethylamino)-ethyl)-2-hydroxy-3,5-dimethyl-N-(2,4,6-trimethyl-3-piperidin-1-yl-phenyl)-benzenesulfonamide | | |

| Example | structure | name | physical description | M + H |
|---|---|---|---|---|
| 157 | 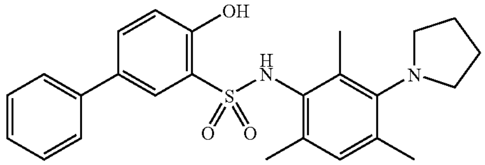 | 4-hydroxy-N-(2,4,6-trimethyl-3-pyrrolidin-1-yl-phenyl)-biphenyl-3-sulfonamide | white solid | 435.0938 M − 1 |
| 158 | 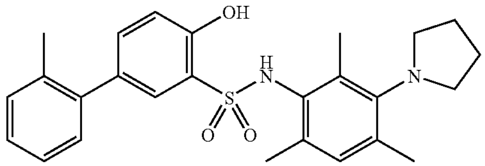 | 4-hydroxy-2'-methyl-N-(2,4,6-trimethyl-3-pyrrolidin-1-yl-phenyl)-biphenyl-3-sulfonamide | colorless film | 449.1259 M − 1 |
| 159 | 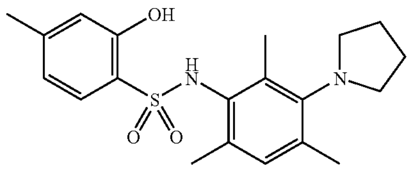 | 2-hydroxy-4-methyl-N-(2,4,6-trimethyl-3-pyrrolidin-1-yl-phenyl)-benzenesulfonamide | white solid | 375.14 |
| 160 | 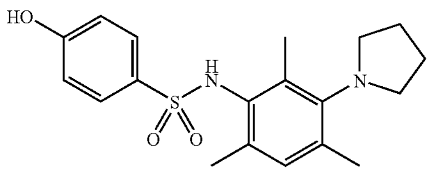 | 4-hydroxy-N-(2,4,6-trimethyl-3-pyrrolidin-1-yl-phenyl)-benzenesulfonamide | white foam | |

EXAMPLE 161

2-Amino-N-(2,4,6-trimethyl-3-pyrrolidin-1-yl-phenyl)-benzesulfonamide (39)

The title compound was synthesized in the same manner as for Example 149 from 38 as a light yellow foam. ESI [M+H$^+$]=360.08.

The compounds of Examples 162-165 are prepared by the procedure of Example 161.

| Example | structure | name | physical description | M + H |
|---|---|---|---|---|
| 161 | 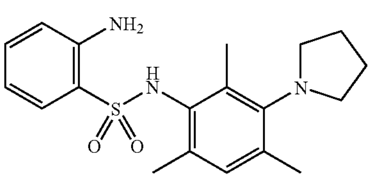 | 2-amino-N-(2,4,6-trimethyl-3-pyrrolidin-1-yl-phenyl)-benzenesulfonamide | light yellow foam | 360.08 |
| 162 | 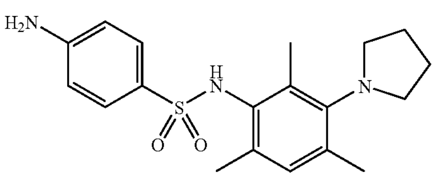 | 4-amino-N-(2,4,6-trimethyl-3-pyrrolidin-1-yl-phenyl)-benzenesulfonamide | yellow foam | |

-continued

| Example | structure | name | physical description | M + H |
|---|---|---|---|---|
| 163 | 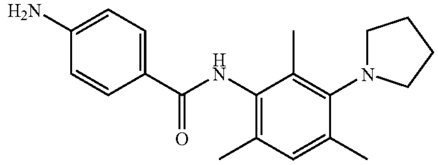 | 4-amino-N-(2,4,6-trimethyl-3-pyrrolidin-1-yl-phenyl)-benzamide | yellow solid | |
| 164 | 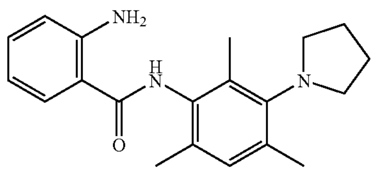 | 2-amino-N-(2,4,6-trimethyl-3-pyrrolidin-1-yl-phenyl)-benzamide | white solid | 324.28 |
| 165 | 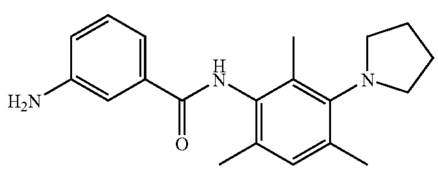 | 3-amino-N-(2,4,6-trimethyl-3-pyrrolidin-1-yl-phenyl)-benzamide | yellow solid | 324.29 |

EXAMPLE 166

4-Hydroxy-N-(2,4,6-trimethyl-3-pyrrolidin-1-yl-phenyl)-benzamide

The title compound, a yellow solid, was synthesized in the same manner as for Example 149 using Example 111 as the substrate for catalytic hydrogenation.

EXAMPLE 167

2-Amino-3,5-dichloro-N-(2,4,6-trimethyl-3-pyrrolidin-1-yl-phenyl)-benzenesulfonamide (40)

To a solution of 39 (0.12 g, 0.32 mmol) in acetic acid (4.0 mL) at 0° C. was added sulfuryl chloride (0.092 g, 0.68 mmol) dropwise. After being stirred at room temperature for 2 h, the reaction mixture was quenched with cold saturated (aq.) NaHCO$_3$ and was extracted with EtOAc (70 mL). The organic layer was washed with sat. NaHCO$_3$, H$_2$O, and brine before it was dried (MgSO$_4$) and evaporated to dryness. The resulting crude product was chromatographed eluting with 10% to 25% EtOAc in hexanes to yield the title compounds as a light-yellow solid (0.11 g, 79%, ESI [M+H$^+$]=428.13).

EXAMPLE 168

4-Amino-3,5-dichloro-N-(2,4,6-trimethyl-3-pyrrolidin-1-yl-phenyl)-benzenesulfonamide The title compound was synthesized in the same manner as for Example 167 using Example 163 as the substrate for chlorination reaction. It was a tan solid ESI [M+H$^+$]=428.11.

EXAMPLE 169

3,5-Dichloro-2-methanesulfonylamino-N-(2,4,6-trimethyl-3-pyrrolidin-1-yl-phenyl)-benzenesulfonamide (42)

To a solution of 40 (69 mg, 0.16 mmol) in DMF at 0° C. was added NaH (60% in mineral oil, 14 mg, 0.35 mmol). The mixture was stirred for 10 min at 0° C. before the addition of methanesulfonyl chloride (22 mg, 0.19 mmol). The resulting mixture was then stirred at room temperature overnight. The reaction was quenched with a few drops of dilute HCl and then diluted with EtOAc (60 mL). The organic layer was washed with water (2×30 mL) and brine (30 mL) and the volatiles were removed by evaporation on a rotavap. The residue was purified on a silica gel column (15% to 30% EtOAc in hexanes) to yield the title compounds as an off-white solid (10 mg ESI [M+H$^+$]=506.12).

EXAMPLE 170

N-(2,4-Dichloro-6-(2,4,6-trimethyl-3-pyrrolidin-1-yl-phenylaminosulfonyl)phenyl)-acetamide (41)

The title compound was synthesized in the same manner as for Example 169 using acetyl chloride instead of methanesulfonyl chloride. It was obtained as an off-white solid (ESI [M−H$^+$]=468.22).

EXAMPLE 171

Tert-Butyl (2-(3,5-dichloro-2-hydroxybenzene-sulfonylamino)-6-piperidin-1-yl-benzyl)-carbamate (47)

1) 2-Amino-6-piperidin-1-yl-benzonitrile (44). A solution of 2-amino-6-fluoro-benzonitrile (844 mg, 6.2 mmol) in piperidine (5 mL) was heated overnight at 80° C. After usual workup, the residue was loaded into column (silica gel) and eluted with hexanes:EtOAc (5:1) to give 450 mg of 44.

2) 2-Amino-6-piperidin-1-yl-benzylamine (44a). To a solution of 44 (260 mg, 1.29 mmol) in anhydrous THF (6 mL) was added lithium aluminum hydride (1 M in THF, 6 mL, 6 mmol). The mixture was heated overnight at 75° C. The reaction was allowed to cool to room temperature and quenched with $Na_2SO_4.10H_2O$ and stirred for 30 min. The solids were filtered off, the filtrate was concentrated on a rotavap to afford 44a (270 mg).

3) tert-Butyl (2-amino-6-piperidin-1-yl-benzyl)-carbamate (45). To a solution of 44a (300 mg, 1.46 mmol) in anhydrous THF (8 mL) was added $Boc_2O$ (351 mg, 1.61 mmol) and the mixture was stirred overnight at room temperature. After usual workup, the residue was loaded into column (silica gel) and eluted with hexanes: EtOAc (7:1) to give 45 (160 mg).

4) The title compound was synthesized according to the protocol shown in Scheme 2 using 45 and 3,5-dichloro-2-hydroxy-benzenesulfonyl chloride (46). It was an off-white solid (ESI ([M+H$^+$]=530.11).

EXAMPLE 172

N-(2-Aminomethyl-3-piperidin-1-yl-phenyl)-3,5-dichloro-2-hydroxy-benzenesulfonamide (48)

To a solution of 47 (75 mg) in dichloromethane (5 mL) was added TFA (0.5 mL). The solution was stirred overnight. Followed by usual workup. The title compound was obtained as an off-white solid (35 mg).

EXAMPLE 173

2-Aminomethyl-N-(2,4,6-trimethyl-3-pyrrolidin-1-yl-phenyl)-benzenesulfonamide

The title compound was synthesized from the corresponding nitrile (Example 103) using the procedure as shown for 44a.

The compounds of Examples 174-175 are prepared by the procebure of Example 13.

| Example | structure | name | physical description | M + H |
|---|---|---|---|---|
| 173 | 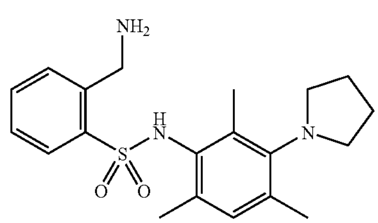 | 2-aminomethyl-N-(2,4,6-trimethyl-3-pyrrolidin-1-yl-phenyl)-benzenesulfonamide | green solid | 373.95 |
| 174 | 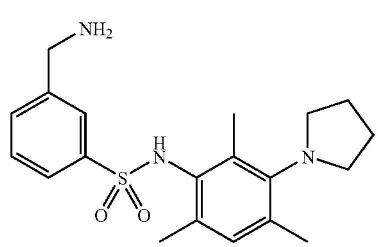 | 3-aminomethyl-N-(2,4,6-trimethyl-3-pyrrolidin-1-yl-phenyl)-benzenesulfonamide | yellow solid | 374.16 |
| 175 | 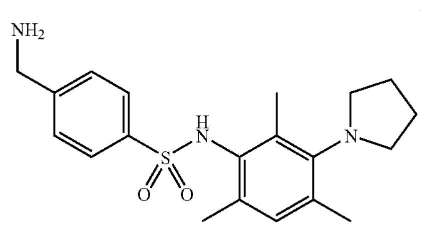 | 4-aminomethyl-N-(2,4,6-trimethyl-3-pyrrolidin-1-yl-phenyl)-benzenesulfonamide | yellow solid | 374.13 |

EXAMPLE 176

3-Phenylaminosulfonyl-N-(2,4,6-trimnethyl-3-pyrrolidin-1-yl-phenyl)-thiophene-2-carboxamide (53)

The title compound was synthesized according to a literature sequence (Wu, et. al. *J. Med. Chem.* 1999, 42, 4485-4499) of sulfonamide coupling/MOM protection/amide coupling/MOM deprotection (Scheme 4) as a yellowish solid ESI [M+H$^+$]=470.2.

EXAMPLE 177

3-Benzenesulfonylamino-N-(2,4,6-trimethyl-3-pyrrolidin-1-yl-phenyl)-thiophene-2-carboxamide (58)

The title compound was synthesized according to the same reaction sequence (Scheme 4) as for Example 176, except that coupling partners were methyl 3-aminothiophene-2-carboxylate (54) and benzenesulfonyl chloride. It was an amber solid ESI [M+H$^+$]=470.15.

EXAMPLE 178

1-(2-Methoxyphenyl)-3-(2,4,6-trimethyl-3-pyrrolidin-1-yl-phenyl)-urea

A solution of 2 (0.25 g, 1.22 mmol) and 2-methoxyphenyl isocyanate (0.18 g, 1.22 mmol) in toluene (5 mL) was heated at 80° C. overnight. The mixture was allowed to cool to room temperature and then diluted with EtOAc. The organic layer was washed with water (50 mL) and brine (50 mL) before it was dried (MgSO$_4$) and concentrated on a rotavap. The residue was chromatographed on silica gel to give the title compound (0.11 g) as a solid. ESI [M+H$^+$]=354.22.

The compounds of Examples 179-184 are prepared by the procedure of Example 178.

| Example | structure | name | physical description | M + H |
|---|---|---|---|---|
| 178 | 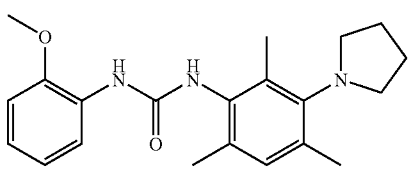 | 1-(2-methoxyphenyl)-3-(2,4,6-trimethyl-3-pyrrolidin-1-yl-phenyl)-urea | | 354.22 |
| 179 | 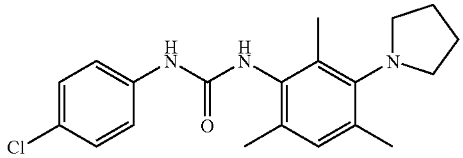 | 1-(4-chlorophenyl)-3-(2,4,6-trimethyl-3-pyrrolidin-1-yl-phenyl)-urea | | 358.17 |
| 180 | 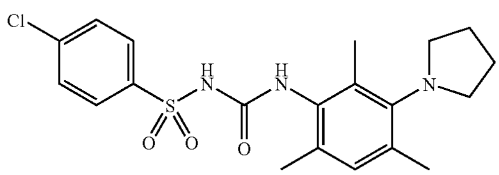 | 1-(4-chlorobenzenesulfonyl)-3-(2,4,6-trimethyl-3-pyrrolidin-1-yl-phenyl)-urea | yellow solid | 421.23 |
| 181 | 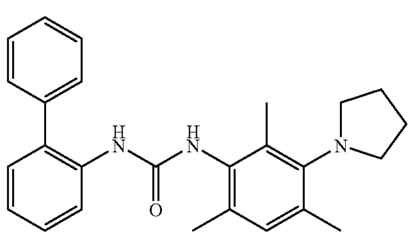 | 1-(biphenyl-2-yl)-3-(2,4,6-trimethyl-3-pyrrolidin-1-yl-phenyl)-urea | yellow foam | 400.29 |
| 182 | 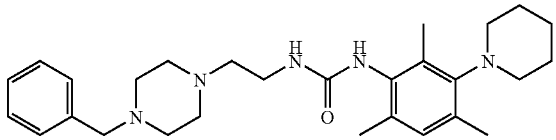 | 1-(2-(4-benzyl-piperazin-1-yl)-ethyl)-3-(2,4,6-trimethyl-3-piperidin-1-yl-phenyl)-urea | | |

| Example | structure | name | physical description | M + H |
|---|---|---|---|---|
| 183 | 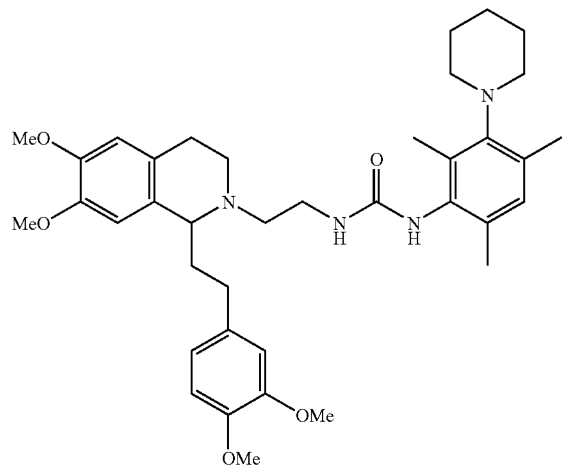 | 1-(2-(1-(2-(3,4-dimethoxy-phenyl)-ethyl)-6,7-dimethoxy-3,4-dihydro-1H-isoquinolin-2-yl)-3-(2,4,6-trimethyl-3-piperidin-1-yl-phenyl)-urea | | |
| 184 | 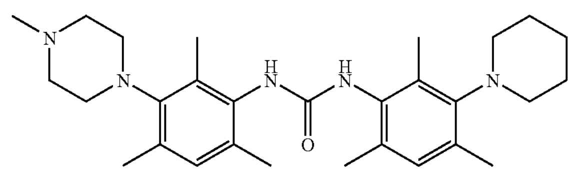 | 1-(2,4,6-trimethyl-3-(4-methyl-piperazin-1-yl)-phenyl)-3-(2,4,6-trimethyl-3-piperidin-1-yl-phenyl)-urea | | |

EXAMPLE 182

1-(2-(4-benzyl-piperazin-1-yl)-ethyl)-3-(2,4,6-trimethyl-3-piperidin-1-yl-phenyl)-urea To a solution of 2,4,6-trimethyl-3-piperazin-1-yl-phenylamine (0.2 g, 0.92 mmol) and Hunig's base (0.7 mL, 4.0 mmol) in anhydrous 1,2-dichloroethane (3 mL) at 0° C. was added triphosgene (0.1 g, 0.35 mmol). The mixture was stirred at 0° C. for 30 minutes before the addition of a solution of 2-(4-benzyl-piperazin-1-yl)-ethylamine (0.2 g, 0.92 mmol) in 1,2-dichloroethane (2 mL). The reaction was stirred overnight and partitioned between water and methylene chloride. The organic layer was washed with brine, dried (MgSO$_4$) and concentrated. The residue was chromatographed with florisil, eluting with a mixture of hexanes and ethyl acetate in the ratio of 2:1 to 100% ethyl acetate, and then to a mixture of ethyl acetate and MeOH (30:1) to give the title compound as a white foam (0.27 g, 64% yield).

EXAMPLE 185

N-benzyl-2-benzyloxy-3,5-dichloro-N-(2,4,6-trimethyl-3-pyrrolidin-1-yl-phenyl)-benzenesulfonamide To a solution of Example 69 (0.10 g, 0.23 mmol) in anhydrous DMF (3 mL) were sequentially added benzyl bromide (0.039 g, 0.23 mmol) and K$_2$CO$_3$ (0.032 g, 0.23 mmol). The mixture was stirred at room temperature overnight and then diluted with EtOAc (70 mL). The organic layer was washed with dilute HCl (30 mL), water (30 mL), and brine (30 mL), and then dried over Na$_2$SO$_4$. The solids were filtered off and the filtrate concentrated on a rotavap. The residue was purified on silica gel (5% to 15% EtOAc in hexanes) to give the product (0.050 g) as a white solid. ESI [M+H$^+$]=609.2.

EXAMPLE 186

N-Benzyl-1-(3,5-dichloro-2-hydroxy-benzenesulfonyl)-N-(2-dimethylamino-ethyl)-pyrrolidine-2-carboxamide To a solution of N-t-Boc-L-proline (2.0 g, 9.29 mmol) in anhydrous DMF (15 mL) were sequentially added N'-benzyl-N,N-dimethylethylendiamine (1.65 g, 9.29 mmol), EDC (2.31 g, 12.0 mmol), and HOBT (1.62 g, 12.0 mmol). The reaction mixture was stirred at room temperature for 3 h before being poured into water (75.0 mL). The resulting solution was extracted with ethyl acetate (50 mL), and the organic layer was separated and washed with 10% sodium bicarbonate (aq. 15 mL). The organic layer was dried over magnesium sulfate and concentrated The residue was treated with 4 N HCl in dioxin (10 mL), and the mixture was stirred at room temperature. The reaction was completed after 20 min and the crude reaction mixture was washed with saturated bicarbonate (aq. 145 mL) (pH=9) and then extracted with ethyl acetate (50 mL). The organic layer was dried over MgSO$_4$, and then concentrated to give a yellow oil (1.5 g). To a solution of this oil (100.0 mg) in anhydrous THF (4 mL) was added triethylamine (0.5 mL) and 3,5-dichloro-2-hydroxybenzenesulfonyl chloride (91.0 mg, 0.36 mmol) in one portion. The reaction mixture was stirred at room temperature and the reaction was monitored by TLC. The reaction was completed after 15 min and water was added to the mixture. The resulting solution was extracted with ethyl acetate and the organic layer was washed with 5% NaHCO$_3$ (10 mL). The organic layer was dried over MgSO$_4$ and then concentrated to give the crude product which was purified by silica gel chromatography using 3% methanol in ethyl acetate as the eluent. The title compound was obtained as an off-white solid (135 mg). ESI [M+H$^+$]=500.16.

The compounds of Examples 187-190 are prepared by the procedure of Example 186.

| Example | structure | name | physical description | M + H |
|---|---|---|---|---|
| 186 | 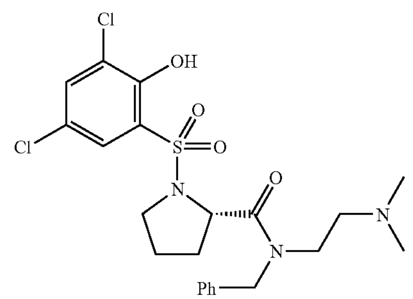 | N-benzyl-1-(3,5-dichloro-2-hydroxy-benzenesulfonyl)-N-(2-dimethylamino-ethyl)-pyrrolidine-2-carboxamide | off-white solid | 500.16 |
| 187 | 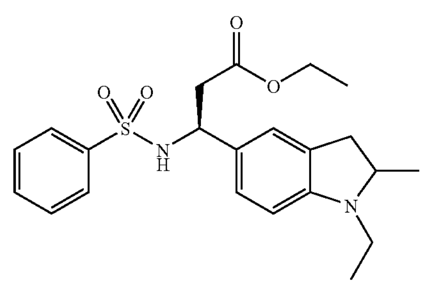 | ethyl 3-benzenesulfonylamino-3-(1-ethyl-2-methyl-2,3-dihydro-1H-indol-5-yl)-propionate | | |
| 188 | 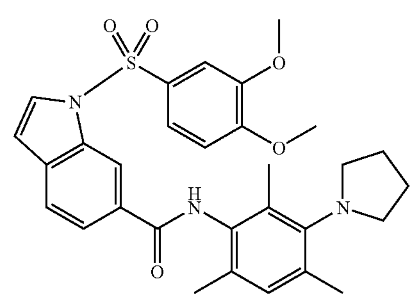 | 1-(3,4-dimethoxy-benzenesulfonyl)-N-(2,4,6-trimethyl-3-pyrrolidin-1-yl-phenyl)-1H-indole-6-carboxamide | white solid | 512.03 |
| 189 | 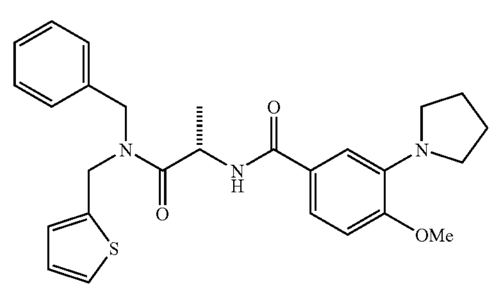 | N-(1-(benzyl-thiophen-2-ylmethyl-aminocarbonyl)-ethyl)-4-methoxy-3-pyrrolidin-1-yl-benzamide | | |
| 190 | 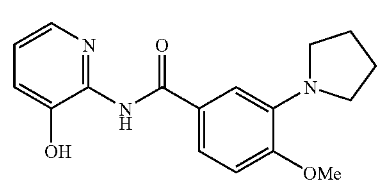 | N-(3-hydroxy-pyridin-2-yl)-4-methoxy-3-pyrrolidin-1-yl-benzamide | beige solid | 314.36 |

EXAMPLE 191

3-Benzenesulfonylamino-N-(2,4,6-trimethyl-3-pyrrolidin-1-yl-phenyl)-benzamide

The title compound was synthesized according to the protocol shown in Scheme 2 using Example 165 and benzenesulfonyl chloride as the starting materials. It was obtained as a yellow solid ESI [M+H$^+$]=464.25.

EXAMPLE 192

3,5-Dichloro-N-(2-cyano-3-piperidin-1-yl-phenyl)-2-hydroxy-benzenesulfonamide

The title compound was synthesized according to the protocol shown in Scheme 2 using 44 and 3,5-dichloro-2-hydroxy-benzenesulfonyl chloride as the starting materials. It was obtained as an off-white solid ESI [M+H$^+$]=423.97.

The CCR-9 antagonist compounds of the present invention may be prepared by the following general procedures:

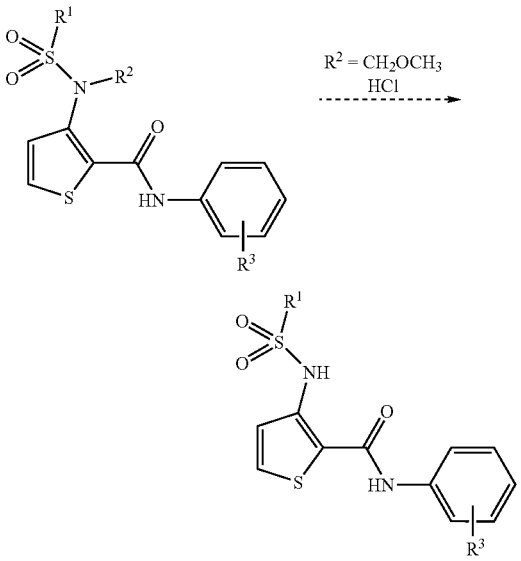

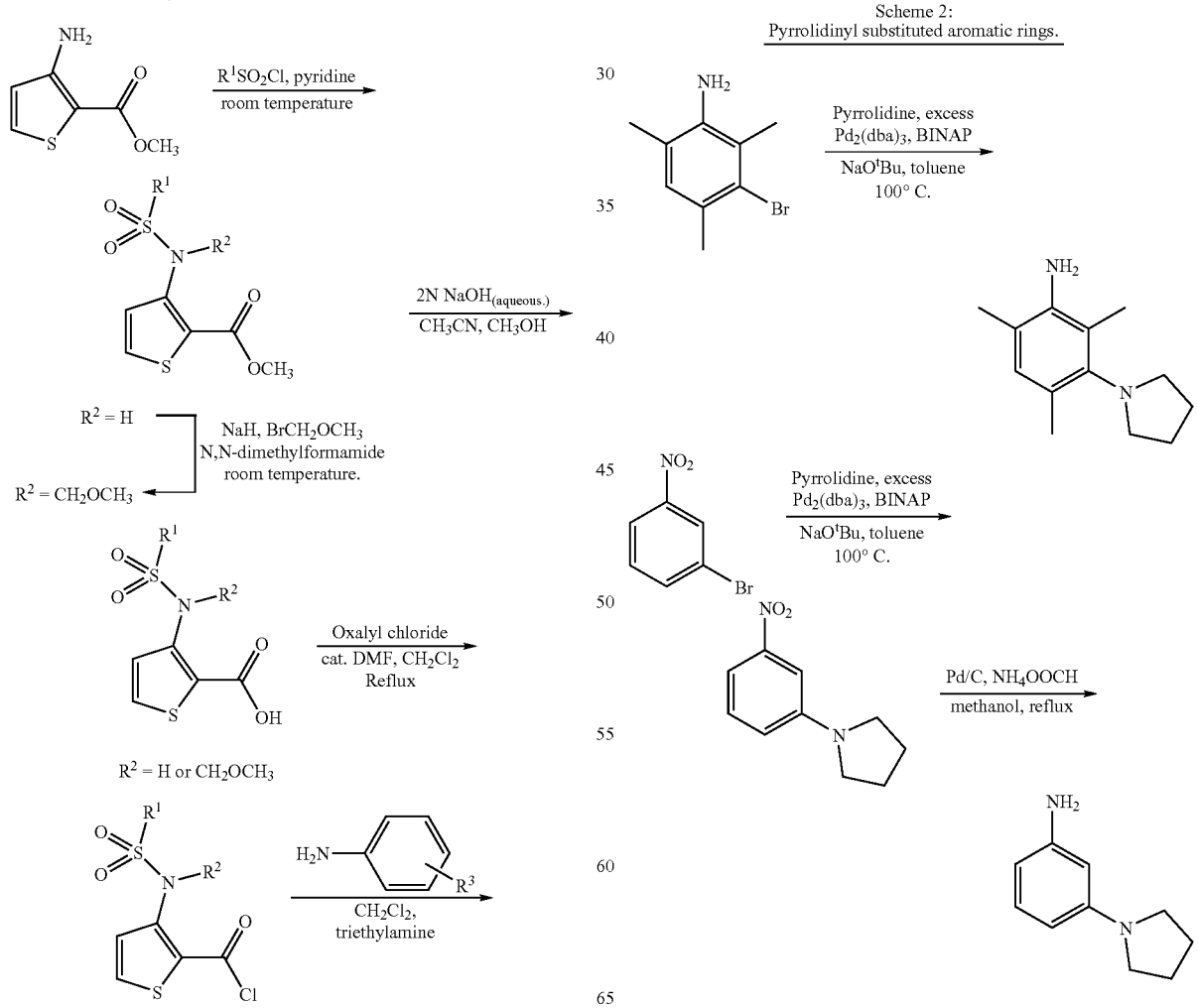

Scheme 3:
Reversal of the Sulfonamide Linkage

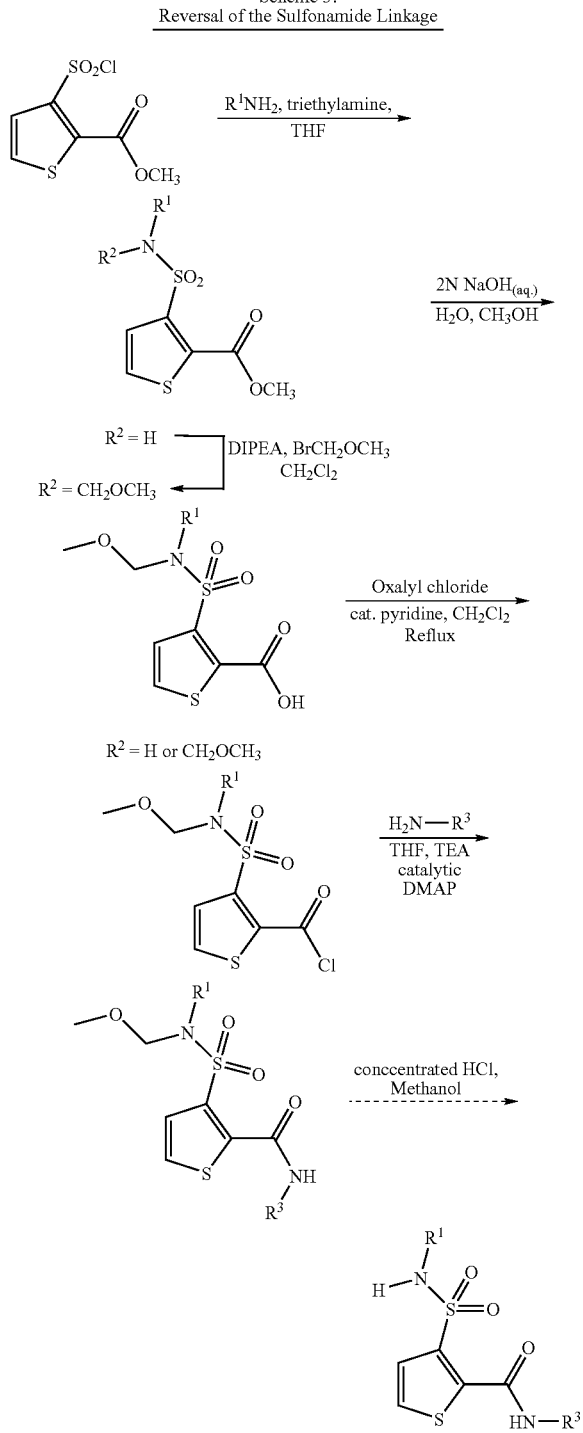

Standard abbreviations include the following:
DMF, N,N-dimethylformamide
THF, Tetrahydrofuran,
TEA, Triethylamine,
DIPEA, N,N-Diisopropyl ethylamine
DMAP, 4-N,N-dimethylaminopyridine,
Pd$_2$(dba)$_3$, Tris(dibenzylideneacetone)dipalladium(0)
BINAP, (+/−)-2,2'-Bis(diphenylphosphino)-1-1'-binaphthyl

EXAMPLE 193

Preparation of Compounds of Scheme 1

Step One

Methyl 3-aminothiophene-2-carboxylate (3.14 g, 20 mmol) was dissolved in pyridine (10 mL) at room temperature. The flask was sealed with a septum and a nitrogen inlet. The solution was treated slowly with a benzenesulfonyl chloride (2.5 mL, 19.5 mmol). The reaction was followed by thin layer chromatography. The reaction was diluted with ethyl acetate and washing with 2N HCl. The organic layer was washed with saturated, aqueous sodium chloride solution and dried over sodium sulfate. The solution was decanted and evaporated under reduced pressure to give 3-benzenesulfonylaminothiophene-2-carboxylic acid methyl ester (5.36 g, 90%), which was used without further purification.

Step Two

3-Benzenesulfonylaminothiophene-2-carboxylic acid methyl ester (1.5 g, 5.0 mmol) was dissolved in acetonitrile (10 mL) and treated with aqueous, sodium hydroxide solution (2N, 7.5 mL, 3 equivalents) at room temperature. The solution was warmed to 50° C. and monitored by thin layer chromatography. Upon completion of the reaction, the mixture was cooled and extracted once with diethyl ether. The ether layer was set aside. The aqueous layer was then acidified with aqueous HCl (2N, excess) before re-extracting twice with ethyl acetate. The combined organic layers were washed once with brine solution and dried over anhydrous sodium sulfate. The ethyl acetate was decanted and evaporated under reduced pressure to give of 3-benzenesulfonylaminothiophene-2-carboxylic acid (1.34 g, 95%) as a white powder.

Step Three

3-Benzenesulfonylaminothiophene-2-carboxylic acid (0.61 g, 2.15 mmol) was suspended in dichloromethane (8.6 mL). The resulting mixture was sequentially treated with N,N-dimethylformamide (1 drop), and, in two portions, oxalyl chloride (0.42 mL, 4.8 mmol). After stirring briefly at room temperature, the foaming subsided and the solution was refluxed until the reaction was complete. The mixture was concentrated to dryness, re-dissolved in dichloromethane, and filtered through very small pad of course silica gel, eluting with dichloromethane. Upon concentration of the eluent, the desired 3-benzenesulfonylaminothiophene-2-carboxylic acid chloride was obtained as a yellow solid (0.32 g, 49%), which was used without further purification.

Step Four

To a solution of 2,4,6-trimethylaniline (70 mg, 0.518 mmol) in dichloromethane (0.20 mL) and triethylamine (72 □L, 0.52 mmol) was added 3-benzenesulfonylamninothiophene-2-carboxylic acid chloride (134 mg, 0.444 mmol). The resulting mixture was allowed to stir overnight at room temperature under a nitrogen atmosphere. The reaction mixture was applied directly to silica gel, (9:1 hexane/ethyl acetate, gradient to 4:1 hexane ethyl acetate). The compound was then precipitated from hexanes and dichloromethane to give 3-benzenesulfonylamino-thiophene-2-carboxylic acid (2,4,6-trimethylphenyl) amide as a white solid (0.028 g, 16%).

The following sulfonyl chlorides may be substituted for benzenesulfonyl chloride of Step One:
4-Acetamidobenzenesulfonyl chloride
4-Acetylbenzenesulfonyl chloride
3-Acetylbenzenesulfonyl chloride
2-Acetylbenzenesulfonyl chloride
2-Biphenylsulfonyl chloride-
3-Biphenylsulfonyl chloride-
4-Biphenylsulfonyl chloride-
3,5-Bis(trifluoromethyl)benzenesulfonyl chloride
4-tert-Butylbenzenesulfonyl chloride
butanesulfonyl chloride
2-Chlorobenzenesulfonyl chloride
3-Chlorobenzenesulfonyl chloride
4-Chlorobenzenesulfonyl chloride
2-Cyanobenzenesulfonyl chloride
3-(Chlorosulfonyl)benzoic acid
5-Chloro-2-fluorobenzenesulfonyl chloride
4-Chloro-2,5-dimethylbenzenesulfonyl chloride
2-Chloro-4-(trifluoromethyl)benzenesulfonyl chloride
2-Chloro-4-fluorobenzenesulfonyl chloride
3-Chloro-4-fluorobenzenesulfonyl chloride
3-Chloro-2-fluorobenzenesulfonyl chloride
2-Chloro-6-methylbenzenesulfonyl chloride
5-Chlorothiophene-2-sulfonyl chloride
cyclopentanesulfonyl chloride
cyclohexanesulfonyl chloride
2,3-Dichlorobenzenesulfonyl chloride
2,4-Dichlorobenzenesulfonyl chloride
2,5-Dichlorobenzenesulfonyl chloride
2,5-Dichlorothiophene-3-sulfonyl chloride
2,5-Dimethoxybenzenesulfonyl chloride
3,4-Dimethoxybenzenesulfonyl chloride
2,6-Dichloro-4-(trifluoromethyl)benzenesulfonyl chloride
2,6-Dichlorobenzenesulfonyl chloride
2,6-Difluorobenzenesulfonyl chloride
3,4-Dichlorobenzenesulfonyl chloride
3,4-Difluorobenzenesulfonyl chloride
3,5-Dichloro-2-hydroxybenzenesulfonyl chloride
3,5-Dichlorobenzenesulfonyl chloride
3,5-Difluorobenzenesulfonyl chloride
4-Ethylbenzenesulfonyl chloride
Ethanesulfonyl chloride
2-Fluorobenzenesulfonyl chloride
3-Fluorobenzenesulfonyl chloride
4-Fluorobenzenesulfonyl chloride
4-Fluoro-2-methylbenzenesulfonyl chloride
3-Fluoro-4-methylbenzenesulfonyl chloride
3-Fluoro-4-methylbenzenesulfonyl chloride
5-Fluoro-2-methylbenzenesulfonyl chloride
Methanesulfonyl chloride
2-Methoxybenzenesulfonyl chloride
3-Methoxybenzenesulfonyl chloride
4-Methoxybenzenesulfonyl chloride
Methanesulfonyl chloride
2-Methoxy-4-methylbenzenesulfonyl chloride
4-Phenoxybenzenesulfonyl chloride
Propanesulfonyl chloride
Quinoline-8-sulfonyl chloride
2-(Trifluoromethyl)benzenesulfonyl chloride
3-(Trifluoromethyl)benzenesulfonyl chloride
4-(Trifluoromethyl)benzenesulfonyl chloride
2-(Trifluoromethoxy)benzenesulfonyl chloride
3-(Trifluoromethoxy)benzenesulfonyl chloride
4-(Trifluoromethoxy)benzenesulfonyl chloride
m-Toluenesulfonyl chloride
p-Toluenesulfonyl chloride
o-toluenesulfonyl chloride
2,4,5-Trichlorobenzenesulfonyl chloride
2,4,6-Triisopropylbenzenesulfonyl chloride
2,3,4-Trifluorobenzenesulfonyl chloride It is also envisioned that the following anilines and amines may be substituted for 2,4,6-trimethylaniline of Step Four:
2,4,6-trimethyl-3-piperidinoaniline
2,6-dimethyl-3-piperidinoaniline
2,4-dimethyl-3-piperidinoaniline
4,6-dimethyl-3-piperidinoaniline
2,6-dimethyl-3-pyrrolidinoaniline
2,4-dimethyl-3-pyrrolidinoaniline
4,6-dimethyl-3-pyrrolidinoaniline
2,4,6-trimnethyl-3-(1-imidazolyl)aniline
2,4,6-trimethyl-3-(1-pyrrolidyl)aniline
2,6-dimethyl-3-(1-pyrrolidyl)aniline
2,4-dimethyl-3-(1-pyrrolidyl)aniline
4,6-dimethyl-3-(1-pyrrolidyl)aniline
2,4,6-trimethyl-3-cyclopentylaniline
2,6-dimethyl-3-cyclopentylaniline
2,4-dimethyl-3-cyclopentylaniline
4,6-dimethyl-3-cyclopentylaniline
2,4,6-trimethyl-3-cyclohexylaniline
2,6-dimethyl-3-cyclohexylaniline
2,4-dimethyl-3-cyclohexylaniline
4,6-dimethyl-3-cyclohexylaniline
2,4,6-trimethyl-3-(N,N-dimethylamino)aniline
2,6-dimethyl-3-(N,N-dimethylamino)aniline
2,4-dimethyl-3-(N,N-dimethylamino)aniline
4,6-dimethyl-3-(N,N-dimethylamino)aniline
Morpholine
Piperazine
Piperidine
Pyrrolidine

EXAMPLE 194

Preparation of Compounds of Scheme 2

Step One

To a solution of 3-bromonitrobenzene (2.02 g, 10 mmol) in toluene (33 mL) and pyrrolidine (1.0 mL, 12 mmol) was added sodium t-butoxide (1.92 g, 20 mmol) and the solution was deoxygenated by passing a nitrogen through the solution at room temperature for 15 minutes. BINAP and tris(dibenzylideneacetone)dipalladium(0) complex were subsequently added as a solid and the nitrogen bubbling was continued for an additional 5 minutes. The mixture was heated at 100° C. overnight. The reaction mixture was then cooled and partitioned between water and ethyl acetate. The organic layer was washed once with brine solution and dried over anhydrous sodium sulfate. The ethyl acetate was decanted and evaporated under reduced pressure to give the desired 1-(3-nitrophenyl)pyrrolidine as a red oil (1.5 g, 79%).

Alternatively, under these conditions, 3-bromo-2,4,6-trimethylaniline may be substituted for 3-bromotoluene to prepare the corresponding 3-pyrrolidino-2,4,6-trimethylaniline, except that the pyrrolidine is increased to 5 equivalents.

Step Two

To a solution of 1-(3-nitrophenyl)pyrrolidine (1.5 g, 7.8 mmol) in methanol (25 mL) was added Pd/C (10%, Degusa type E101, 50% water, 1 g) and ammonium formate (0.96 g, 15 mmol). The resulting suspension was heated at reflux until the reaction was complete. The mixture was filtered through celite and concentrated under reduced pressure filtered through course silica gel with ethyl acetate to give the desired product 3-(1-pyrrolidino)aniline (0.65 g, 79%).

EXAMPLE 195

Preparation of Compounds of Scheme 3

Step One

To a solution of an aniline (1.02 g, 10.9 mmol, 1.1 equivalents) dissolved in dry THF (35 mL) and triethylamine (1.53 mL, 1.1 equivalents) at room temperature, sealed with a septum and a nitrogen inlet, was added 2-carbomethoxythiophene-3-sulfonyl chloride (2.5 g, 9.9 mmol, 95% purity). The reaction mixture was stirred at room temperature over night. Upon completion, the reaction will be extracted by diluting with ethyl acetate and washing with aqueous HCl (2N), water and saturated, aqueous sodium chloride solution. The organic layer was dried over sodium sulfate. The solution will be decanted and evaporated under reduced pressure to give the desired 3-phenylsulfamoylthiophene-2-carboxylic acid methyl ester (2.6 g, 88%).

Step Two

The Sulfonamide of Step One, 3-phenylsulfamoylthiophene-2-carboxylic acid methyl ester, was dissolved in dry dichloromethane and N,N-diisopropyl ethylamine. The resulting mixture was chilled to 0° C. prior to the addition of bromomethyl methyl ether. The reaction mixture was stirred over night at room temperature. The mixture was partitioned between dichloromethane and aqueous HCl (2N). The organic layer will then be washed one time with saturated sodium chloride solution and dried over sodium sulfate, followed by concentration to dryness under reduced pressure to give the desired product, 3-(N-methoxymethyl-N-phenylsulfamoyl)thiophene-2-carboxylic acid methyl ester (3 g, quantitative).

Step Three

To a homogenous mixture of 3-(N-methoxymethyl-N-phenylsulfamoyl)thiophene-2-carboxylic acid methyl ester (3 g, 8.75 mmol) in methanol and water was added aqueous, sodium hydroxide solution (2N, excess) at room temperature. Upon completion of the reaction, the mixture was cooled and extracted once with diethyl ether. The aqueous layer will then acidified with aqueous, HCl (2N, excess) before re-extracting twice with ethyl acetate. The organic layer was washed once with brine solution and dried over anhydrous sodium sulfate. The ethyl acetate solution was decanted and evaporated under reduced pressure to give the desired 3-(N-methoxymethyl-N-phenylsulfamoyl) thiophene-2-carboxylic acid (2.2 g, 79%).

Step Four

The 3-(N-methoxymethyl-N-phenylsulfamoyl)thiophene-2-carboxylic acid of step three (0.722, 2.2 mmol) was suspended in dichloromethane (5 mL), followed by sequentially treating with pyridine (1 drop) and chilled to 0° C. The solution was then treated with oxalyl chloride (2.43 mL, 2M in dichloromethane) before refluxing for 1 hour. The mixture was cooled to room temperature and concentrated to dryness under reduced pressure. The residue was re-dissolved in tetrahydrofuran (5 mL) and added to a cold (0° C.) solution of 3-pyrrolidino-2,4,6-trimethylaniline (0.250 g, 1.2 mmol) in tetrahydrofuran (4 mL), triethylamine(0.36 mL 2.6 mmol) and 4-dimethylaminopyridine (0.027 g, 10 mol %). The reaction mixture was allowed to stir at room temperature over night. The material was purified by normal phase (SiO$_2$) chromatography by eluting with 3:1 hexanes:ethyl acetate to give 3-(N-methoxymethyl-N-phenylsulfamoyl) thiophene-2-carboxylic acid) (107 mg, 15%).

Step Five 3-(N-methoxymethyl-N-phenylsulfamoyl)thiophene-2-carboxylic acid (107 mg, 0.331 mmol) of the previous step was dissolved in methanol and treated with a concentrated HCl (9 mL). The reaction mixture was heated to 70° C. for 2.5 hours, cooled and poured onto ice water. The pH was adjusted to 3-4, and the aqueous mixture was extracted with ethyl acetate. The organic layer was washed with saturated sodium chloride solution and dried over sodium sulfate before concentrating to dryness under reduced pressure to give the desired product such as 3-phenylsulfamoylthiophene-carboxylic acid(2,4,6-trimethylphenyl) amide (40 mg, 26%).

The invention claimed is:
1. A compound of the formula:

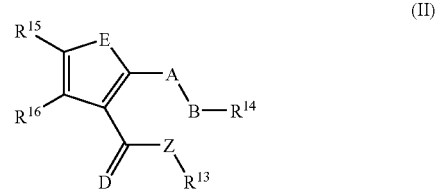

(II)

where E is S;

D is O or S;

Z is NR$^{13a}$, where R$^{13a}$ is H or lower alkyl;

A is NR$^{17}$ or SO$_2$, where R$^{17}$ is H, alkyl or aryl when A is NR$^{17}$, B is SO$_2$; when A is SO$_2$, B is NR$^{19}$, where R$^{19}$ is H alkyl or aryl;

R$^{14}$ is phenyl;

R$^{13}$ is phenyl; and

R$^{15}$ and R$^{16}$ are independently H, alkyl, aryl, heteroaryl, halogen, hydroxy, alkoxy or NR$_2^{21}$, where R$^{21}$ is H, alkyl, aryl or heteroaryl, and the pharmaceutically acceptable salts thereof, wherein the alkyl, heteroaryl and alkoxy groups are unsubstituted or substituted with one or more groups selected from alcohol, ether, ester, amide, sulfone, sulfide, hydroxyl, nitro, cyano, carboxy, amine, heteroatom, lower alkyl, lower alkoxy, lower alkoxycarbonyl, alkoxyalkoxy, acyloxy, halogen, trifluoromethoxy, trifluoromethyl, alkyl, aralkyl, alkenyl, alkynyl, aryl, cyano, carboxy, carboalkoxy, carboxyalkyl, cycloalkyl, cycloalkylalkyl, heterocyclyl, alkylbeterocyclyl, heterocyclylalkyl, oxo, arylsulfonyl and aralkylaminocarbonyl;

R$^{14}$ is substituted with unsubstituted or substituted with one or more groups selected from alcohol, ether, ester, amide, sulfone, sulfide, hydroxyl, nitro, cyano, carboxy, amine, heteroatom, lower alkyl, lower alkoxy, lower alkoxycarbonyl, alkoxyalkoxy, acyloxy, halogen, trifluoromethoxy, trifluoromethyl, alkyl, aralkyl, alkenyl, alkynyl, aryl, cyano, carboxy, carboalkoxy, carboxyalkyl, cycloalkyl, cycloalkylalkyl, heterocyclyl, alkylbeterocyclyl, heterocyclylalkyl, oxo, arylsulfonyl and aralkylaminocarbonyl; and R$^{13}$ is substituted with lower alkyl and heterocyclyl.

2. A pharmaceutical composition comprising a compound of claim 1 and a pharmaceutically acceptable carrier or excipient.
3. A compound selected from a group consisting of:
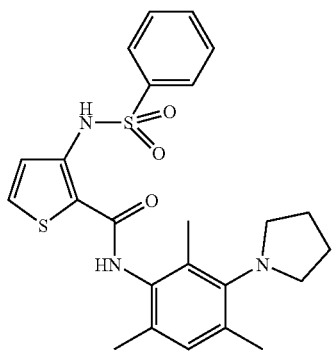
and
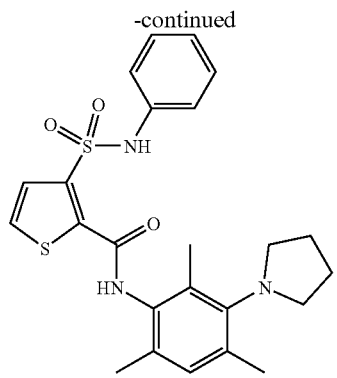
4. A pharmaceutical composition comprising a compound of claim 3 and a pharmaceutically acceptable carrier or excipient.
* * * * *